(12) United States Patent
Schomburg et al.

(10) Patent No.: US 10,126,310 B2
(45) Date of Patent: Nov. 13, 2018

(54) NUCLEOSOME SUBSTRATE ASSAYS

(71) Applicant: Proteros Biostructures GMBH, Martinsried (DE)

(72) Inventors: Adrian Schomburg, Gräfelfing (DE); Robert Van Der Burgh, Munich (DE)

(73) Assignee: PROTEROS BIOSTRUCTURES GMBH, Martinsried (DE)

( * ) Notice: Subject to any disclaimer, the term of this patent is extended or adjusted under 35 U.S.C. 154(b) by 132 days.

(21) Appl. No.: 15/111,461

(22) PCT Filed: Jan. 13, 2015

(86) PCT No.: PCT/EP2015/050515
§ 371 (c)(1),
(2) Date: Jul. 13, 2016

(87) PCT Pub. No.: WO2015/104431
PCT Pub. Date: Jul. 16, 2015

(65) Prior Publication Data
US 2017/0122964 A1 May 4, 2017

(30) Foreign Application Priority Data
Jan. 13, 2014 (GB) .................. 1400522.7

(51) Int. Cl.
*G01N 33/542* (2006.01)
*G01N 33/68* (2006.01)
*G01N 33/573* (2006.01)
*G01N 33/58* (2006.01)
*G01N 21/64* (2006.01)

(52) U.S. Cl.
CPC ..... *G01N 33/6875* (2013.01); *G01N 21/6428* (2013.01); *G01N 33/542* (2013.01); *G01N 33/573* (2013.01); *G01N 33/582* (2013.01); *G01N 2021/6432* (2013.01)

(58) Field of Classification Search
None
See application file for complete search history.

(56) References Cited

U.S. PATENT DOCUMENTS

2008/0199964 A1    8/2008  Shokat et al.
2011/0021362 A1*   1/2011  Trojer .................. C12Q 1/26
                                                     506/7

FOREIGN PATENT DOCUMENTS

WO    2008/033992 A2    3/2008
WO    2013/184930 A2   12/2013

OTHER PUBLICATIONS

Yu et al. (J. Biomolecular Screening vol. 17, p. 27-38) (Year: 2012).*
Mercurio et al. Chapter 4 "Alterations of Histone Modifications in Cancer" (from Epigenetics in Human Diseases edited byTrygve Tollefsbol total 35 pages) (Year: 2012).*
Benvenuto et al., "The Photomorphogenesis Regulator DET1 Binds the Amino-Terminal Tail of Histone H2B in a Nucleosome Context", Current Biology, vol. 12, Sep. 3, 2002, pp. 1529-1534.
Blosser, et al., "Dynamics of Nucleosome Remodelling by Individual ACF Complexes", Nature, vol. 462, No. 7276, Dec. 24, 2009, pp. 1022-1027.
Buning et al., "Single-Pair Fret Experiments on Nucleosome Conformational Dynamics", Biochimie, vol. 92, 2010, pp. 1729-1740.
Chatterjee et al., "Chemical Approaches for Studying Histone Modifications", The Journal of Biological Chemistry, vol. 285, No. 15, Apr. 9, 2010, pp. 11045-11050.
Fierz et al., "Stability of Nucleosomes Containing Homogenously Ubiquitylated H2A and H2B Prepared Using Semisynthesis", Journal of the American Chemical Society, vol. 134, 2012, pp. 19548-19551.
International Preliminary Report on Patentability received for PCT Patent Application No. PCT/EP2015/050515, dated Jul. 28, 2016, 8 pages.
International Search Report and Written Opinion received for PCT Patent Application No. PCT/EP2015/050515, dated May 7, 2015, 13 pages.
Le et al., "Site-Specific and Regiospecific Installation of Methylarginine Analogues into Recombinant Histones and Insights into Effector Protein Binding", Journal of the American Chemical Society, vol. 135, 2013, pp. 2879-2882.
Machleidt et al., "TR-FRET Cellular Assays for Interrogating Posttranslational Modifications of Histone H3", Journal of Biomolecular Screening, vol. 16, No. 10, 2011, pp. 1236-1246.
Neumann et al., "A Method for Genetically Installing Site-Specific Acetylation in Recombinant Histones Defines the Effects of H3 K56 Acetylation", Molecular Cell, vol. 36, Oct. 9, 2009, pp. 153-163.
Nikolov et al., "Systematic Analysis of Histone Modification Readout", Molecular Biosystems, vol. 9, 2013, pp. 182-194.
North et al., "Regulation of the Nucleosome Unwrapping Rate Controls DNA Accessibility", Nucleic Acids Research, vol. 40, No. 20, Sep. 9, 2012, pp. 10215-10227.
Petesch et al., "Overcoming the Nucleosome Barrier during Transcript Elongation", Trends in Genetics, vol. 28, No. 6, Jun. 1, 2012, pp. 285-294.
Poirier et al., "Dynamics and Function of Compact Nucleosome Arrays", Nature Structural & Molecular Biology, vol. 16, No. 9, Sep. 2009, pp. 938-944.
Ruthenburg et al., "Recognition of a Mononucleosomal Histone Modification Pattern by BPTF Via Multivalent Interactions", Cell, vol. 145, May 27, 2011, pp. 692-706.

(Continued)

*Primary Examiner* — Changhwa J Cheu
(74) *Attorney, Agent, or Firm* — Morrison & Foerster LLP

(57) ABSTRACT

The present invention relates to methods for determining a binding and/or functional interaction of a protein of interest with a nucleosomal substrate wherein at least one of the histone types of the nucleosomal substrate has a homogenous post-translational modification pattern. Further, the invention relates to nucleosomal substrates, wherein at least one of the histone types of the nucleosomal substrate has a homogenous post-translational modification pattern, and to methods for providing such nucleosomal substrates.

15 Claims, 6 Drawing Sheets

Specification includes a Sequence Listing.

(56) References Cited

OTHER PUBLICATIONS

Shimko et al., "Preparation of Fully Synthetic Histone H3 Reveals that Acetyl-Lysine 56 Facilitates Protein Binding within Nucleosomes", Journal of Molecular Biology, vol. 408, 2011, pp. 187-204.
Shogren-Knaak et al., "Histone H4-K16 Acetylation Controls Chromatin Structure and Protein Interactions", Science 2006, vol. 311, Feb. 2006, pp. 844-847.
Simon et al., "Histone Fold Modifications Control Nucieosome Unwrapping and Disassembly", Proceedings of the National Academy of Sciences, vol. 108, No. 31, Aug. 2, 2011, pp. 12711-12716.
Hellwig et al., "Dynamics of CENP-N kinetochore binding during the cell cycle", Journal of Cell Science, 124:3871-3883, 2011.
Winkler et al., "Quantifying Chromatin-Associated Interactions: The HI-FI System", Methods in Enzymology, 512:243-273, 2012.

* cited by examiner

FRET

SEQUENCE LISTING

```
<160> NUMBER OF SEQ ID NOS: 8

<210> SEQ ID NO 1
<211> LENGTH: 201
<212> TYPE: DNA
<213> ORGANISM: Artificial Sequence
<220> FEATURE:
<223> OTHER INFORMATION: nucleosome positioning sequence

<400> SEQUENCE: 1
cctggagaat cccggtgccg aggccgctca attggtcgta gcaagctcta gcaccgctta    60
```

```
aacgcacgta cgcgctgtcc cccgcgtttt aaccgccaag gggattactc cctagtctcc      120
aggcacgtgt cagatatata catcctgtgc atgtattgaa cagcgactcg ggttatgtga      180
tggaccctat acgcggccgc c                                                201

<210> SEQ ID NO 2
<211> LENGTH: 209
<212> TYPE: DNA
<213> ORGANISM: Lytechinus variegatus

<400> SEQUENCE: 2
ggaattccaa cgaataactt ccagggattt ataagccgat gacgtcataa catccctgac       60
cctttaaata gcttaacttt catcaagcaa gagcctacga ccataccatg ctgaatatac      120
cggttctcgt ccgatcaccg aagtcaagca gcatagggct cggttagtac ttggatggga      180
gaccgcctgg gaataccgaa ttccccgag                                         209

<210> SEQ ID NO 3
<211> LENGTH: 207
<212> TYPE: DNA
<213> ORGANISM: Artificial Sequence
<220> FEATURE:
<223> OTHER INFORMATION: control template

<400> SEQUENCE: 3
gttatgtgat ggaccctata cgcggccgcc ctggagaatc ccggtgccga ggccgctcaa       60
ttggtcgtag caagctctag caccgcttaa acgcacgtac gcgctgtccc ccgcgtttta      120
accgccaagg ggattactcc ctagtctcca ggcacgtgtc agatatatac atcctgtgca      180
tgtattgaac agcgactcgg gttatgt                                           207

<210> SEQ ID NO 4
<211> LENGTH: 207
<212> TYPE: DNA
<213> ORGANISM: Artificial Sequence
<220> FEATURE:
<223> OTHER INFORMATION: remodeling template

<400> SEQUENCE: 4
ctggagaatc ccggtgccga ggccgctcaa ttggtcgtag caagctctag caccgcttaa       60
acgcacgtac gcgctgtccc ccgcgtttta accgccaagg ggattactcc ctagtctcca      120
ggcacgtgtc agatatatac atcctgtgca tgtattgaac agcgactcgg gttatgtgat      180
ggaccctata cgcggccgcc ctggaga                                           207

<210> SEQ ID NO 5
<211> LENGTH: 23
<212> TYPE: DNA
<213> ORGANISM: Artificial Sequence
<220> FEATURE:
<223> OTHER INFORMATION: control primer forward

<400> SEQUENCE: 5
gttatgtgat ggaccctata cgc                                                23

<210> SEQ ID NO 6
<211> LENGTH: 22
<212> TYPE: DNA
<213> ORGANISM: Artificial Sequence
<220> FEATURE:
<223> OTHER INFORMATION: control primer rev
```

```
<400> SEQUENCE: 6
acataacccg agtcgctgtt ca                                      22

<210> SEQ ID NO 7
<211> LENGTH: 18
<212> TYPE: DNA
<213> ORGANISM: Artificial Sequence
<220> FEATURE:
<223> OTHER INFORMATION: remodeling template primer fw

<400> SEQUENCE: 7
ctggagaatc ccggtgcc                                           18

<210> SEQ ID NO 8
<211> LENGTH: 15
<212> TYPE: DNA
<213> ORGANISM: Artificial Sequence
<220> FEATURE:
<223> OTHER INFORMATION: remodeling template primer rev

<400> SEQUENCE: 8
tctccagggc gaccg                                              15
```

US 10,126,310 B2

NUCLEOSOME SUBSTRATE ASSAYS

CROSS REFERENCE TO RELATED APPLICATIONS

This is a U.S. National Phase patent application of PCT/EP2015/050515, filed on Jan. 13, 2015, which claims priority to GB 1400522.7, filed on Jan. 13, 2014, all of which are hereby incorporated by reference in the present disclosure in their entirety.

SUBMISSION OF SEQUENCE LISTING AS ASCII TEXT FILE

The content of the following submission on ASCII text file is incorporated herein by reference in its entirety: a computer readable form (CRF) of the Sequence Listing (file name: 7175120006.00SeqList.txt, date recorded: Jul. 13, 2016, size: 3 KB).

FIELD OF THE INVENTION

The present invention relates to methods for determining a binding and/or functional interaction of a protein of interest with a nucleosomal substrate wherein at least one of the histone types of the nucleosomal substrate has a homogenous post-translational modification pattern. Further, the invention relates to nucleosomal substrates, wherein at least one of the histone types of the nucleosomal substrate has a homogenous post-translational modification pattern, and to methods for providing such nucleosomal substrates.

BACKGROUND OF THE INVENTION

Current methods to study proteins involved in epigenetic gene regulation mainly use isolated histone N- or C terminal tail peptides, full length histone dimers, tetramers or octamers from natural sources such as cells of animal, plant or fungal origin or from recombinant sources such as artificial overexpression in *E.coli* or other expression hosts or purified mono- or oligonucleosomes from tissue or cell culture. However, some of these histone subunits do not correspond to the physiological substrate of the epigenetic gene regulation enzymes. Others, such as purified mono- or oligonucleosomes have a heterogeneous post-translation modification pattern which does not allow for a robust and clear readout with respect to post-translational modifying enzyme function. So far, the provision of mono- and oligonucleosomes with a homogenous modification pattern in high yields has been a bottle-neck. Therefore, there is still a need for a sensitive, robust and/or scalable assay for determining the binding and/or functional interaction of post-translational modification proteins.

SUMMARY OF THE INVENTION

One aspect of the invention relates to a method for determining a binding and/or functional interaction of a protein of interest with a nucleosomal substrate comprising DNA wrapped around histone octamers, wherein the method comprises the following steps:
(a) forming a composition of matter comprising the protein of interest and the nucleosomal substrate;
(b) determining a value indicative for the binding and/or functional interaction of the protein of interest with the nucleosomal substrate;
wherein at least one histone type of the nucleosomal substrate has a homogenous post-translational modification pattern.

In one embodiment of the invention the value indicative for the binding and/or functional interaction is determined by optical detection, optionally fluorescent detection.

In a specific embodiment, fluorescent detection is FRET detection, optionally TR-FRET detection.

In one embodiment, the composition of matter further comprises a molecule which is a candidate for modulating the binding and/or functional interaction of the protein of interest with the nucicosomal substrate.

A further aspect of the invention refers to a method for determining the compaction state of a nucleosomal substrate comprising DNA wrapped around histone octamers, wherein the method comprises the following steps:
(a) providing the nucicosomal substrate which is labeled by both a FRET donor and a FRET acceptor;
(b) determining a value indicative for the compaction state of a nucleosomal substrate by FRET detection;
wherein at least one histone type of the nucleosomal substrate has a homogenous post-translational modification pattern.

In a specific embodiment the value indicative for the compaction state of a nucleosomal substrate is determined by TR-FRET detection.

In a particular embodiment, each of the histone types has a homogenous post-translational modification pattern.

Usually, the DNA wrapped around histone octamers is arranged in mononucleosomes and/or oligonucleosomes.

Typically, the method is carried out in medium to high through-put format, optionally in high through-put format. For example, the method is carried out in 96, 384 or 1536 well plates.

In one embodiment, the nucleosomal substrate is labeled. Optionally, the DNA and/or the histones of the nucleosomal substrate are labeled.

In a specific embodiment, the value indicative for the binding and/or functional interaction depends on the compaction state of the nucleosomal substrate.

Usually, the protein of interest is labeled with a fluorescent label.

In one embodiment, the protein of interest is labeled with a FRET acceptor and the nucleosomal substrate is labeled with a corresponding FRET donor.

In another embodiment, the protein of interest is labeled with a FRET donor and the nucleosomal substrate is labeled with a corresponding FRET acceptor.

In a further embodiment, the composition of matter further comprises a reporter protein capable of recognizing a histone having a post-translational modification.

Typically, the reporter protein is an antibody or a histone binding domain.

In this embodiment, the reporter protein is usually labeled, e.g. fluorescently labeled.

In a specific embodiment, the reporter protein is labeled with a FRET acceptor and the nucleosomal substrate is labeled with a corresponding FRET donor, or the reporter protein is labeled with a FRET donor and the nucleosomal substrate is labeled with a corresponding FRET acceptor.

Usually, the protein of interest is an epigenetic regulator. Typically, the epigenetic regulator is a post-translational modifier.

In one embodiment, step (a) is preceded by a step of providing the nucleosomal substrate.

In another embodiment, the nucicosomal substrate is provided as described below.

A further aspect of the invention relates to a method for providing a nucleosomal substrate comprising DNA wrapped around histone octamers, wherein the method comprises the following steps:

(a) providing histone octamers wherein at least one of the histone types of the histone octamer has a homogenous post-translational modification pattern;

(b) combining DNA with the histone octamers thereby obtaining the nucicosomal substrate.

In one embodiment, the method further comprises labeling the nucicosomal substrate.

In a specific embodiment, labeling the nucleosomal substrate comprises labeling DNA, optionally via PCR optionally via PCR and/or by ligation of labeled oligonucleotides, and/or labeling at least one of the histone types;

In another embodiment, the at least one histone type having a homogenous post-translational modification pattern is provided by total chemical synthesis.

In a further embodiment, at least one histone type having a homogenous post-translational modification pattern is provided by site-specific incorporation of an amino acid analogue, optionally by site-specific incorporation of a methyl lysine analogue and/or an acetyl-lysine analogue. Typically a methyl lysine analogue is incorporated.

Usually, the at least one histone type having a homogenous post-translational modification pattern is provided by the method comprising the following the steps:

(i) providing truncated histones of a histone type;

(ii) providing peptides having a homogenous post-translational modification pattern;

(iii) ligating the truncated histones of step (i) and the peptides of step (ii).

In a specific embodiment, step (i) comprises site-specific incorporation of an amino acid analogue, optionally site-specific incorporation of a methyl lysine analogue and/or acetyl-lysine analogue.

In another specific embodiment, step (i) comprises site-specific incorporation of a methyl lysine analogue.

In a further embodiment, in step (ii) the peptide is produced by chemical synthesis.

Usually, the truncated histone comprises an affinity tag and/or a fluorescent tag.

Typically, the truncated histone is truncated at the C-terminal region and the peptide comprises a C-terminal region of the full-length histone. Alternatively, the truncated histone is truncated at the N-terminus and the peptide comprises an N-terminal region of the full-length histone.

Typically, the peptide comprises a histone tail peptide.

A further aspect of the invention relates to nucleosomal substrate comprising DNA wrapped around histone octamers, wherein at least one histone type of the nucleosomal substrate has a homogenous post-translational modification pattern.

In a specific embodiment, each of the histone types has a homogenous post-translational modification pattern.

In one embodiment, the DNA sequence is predetermined.

Usually, the DNA wrapped around histone octamers is arranged in mononucleosomes and/or oligonucleosomes.

Typically, the nucleosomal substrate is fluorescently labeled. Optionally, DNA and/or at least one of the histone types is fluorescently labeled.

In particular, the invention relates to a method for determining a binding and/or functional interaction of a protein of interest with a nucleosomal substrate comprising DNA wrapped around histone octamers, wherein the method comprises the following steps:

(a) forming a composition of matter comprising the protein of interest and the nucleosomal substrate;

(b) determining a value indicative for the binding and/or functional interaction of the protein of interest with the nucleosomal substrate by FRET detection;

wherein at least one histone type of the nucleosomal substrate has a homogenous post-translational modification pattern.

In a specific embodiment the fluorescent detection is TR-FRET detection.

In another embodiment, the composition of matter further comprises a molecule which is a candidate for modulating the binding and/or functional interaction of the protein of interest with the nucleosomal substrate.

In an additional embodiment, the DNA wrapped around histone octamers is arranged in oligonucleosomes.

In a further embodiment the nucleosomal substrate is labeled with a FRET donor and/or FRET acceptor.

In a specific embodiment the DNA of the nucleosomal substrate is labeled with a FRET donor and/or FRET acceptor.

Further or alternatively the histones of the nucleosomal substrate are labeled with a FRET donor and/or FRET acceptor.

In an additional embodiment, the protein of interest is labeled with a FRET acceptor and the nucleosomal substrate is labeled with a corresponding FRET donor or wherein the protein of interest is labeled with a FRET donor and the nucleosomal substrate is labeled with a corresponding FRET acceptor.

In another embodiment, the composition of matter further comprises a reporter protein capable of recognizing a histone having a post-translational modification.

In a specific embodiment, the reporter protein is an antibody.

In another embodiment, the reporter protein is a histone binding protein .

In a further embodiment, the histone binding protein is a histone binding domain or a protein containing a histone binding domain.

Typically, the histone binding domain is a BROMO-, CHROMO- and/or PHD finger domain.

In an additional embodiment the histone binding protein is selected from the group comprising MLL1/2, MLL3/4, SMYD3, USP22, G9A, HP1, JMJD2a, JMJD2c, BRD4, SMARCA2, p300, EZH2, JARID1a, JARID1b, SetD8, PADI4, PHF8, PRMT5, SctDB8, NSD1, NSD2, NSD3, FBXL10, JMJD3, Dot1L, LSD1, HDAC1-11, Sirtuin 1-7, Tip60, PCAF, UTX, EZH1, PRMT3, PRMT4 and USP16.

In a preferred embodiment the histone binding protein is preferably selected from the group comprising EZH2, SMYD3, JMJD3, BRD4, NSD2, LSD1, HDAC2 and HDAC6.

In another embodiment, the reporter protein is labeled with a FRET acceptor and the nucleosomal substrate is labeled with a corresponding FRET donor, or the reporter protein is labeled with a FRET donor and the nucleosomal substrate is labeled with a corresponding FRET acceptor.

In a specific embodiment, the value indicative for the binding and/or functional interaction depends on the compaction state of the nucleosomal substrate.

In a further embodiment, both FRET acceptor and FRET donor are located on the nucleosomal substrate.

In another specific embodiment, the FRET donor is located at the DNA and the FRET acceptor is located at the histone.

In another embodiment, several nucleosomes of an oligonucleosomes are labeled.

Nucleosomes sediment at 11S as expected and the homogeneity of the sample is high.

Figure 2:
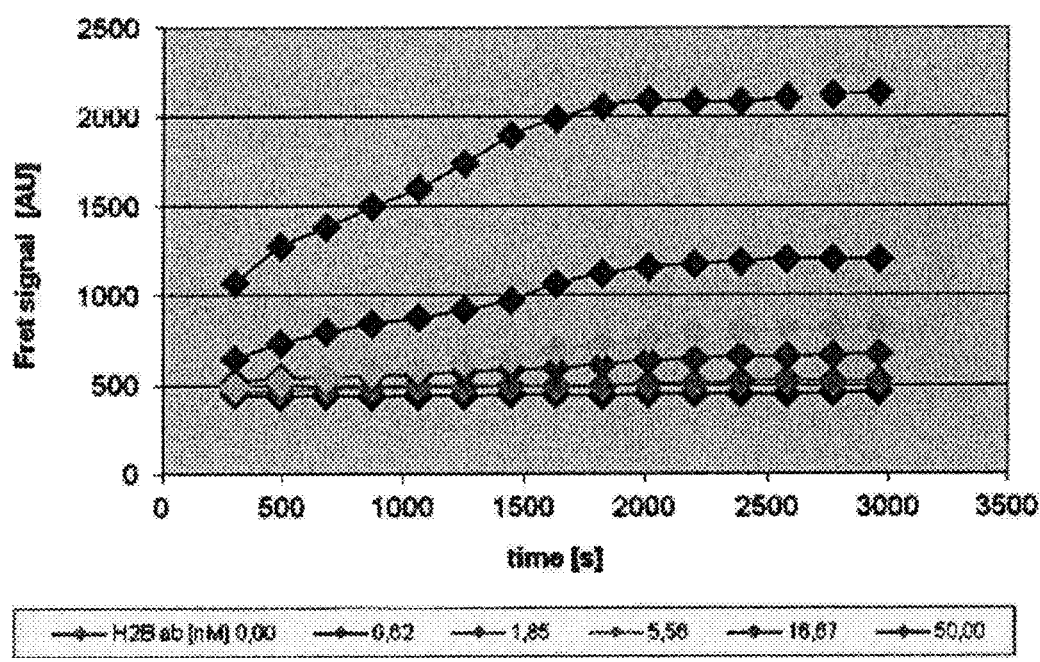

FIG. 2. FRET signal over time at 2.22 nm nucleosome concentration, 16 nm GST-Tb antibody, 7 nm LSD1 and increasing concentrations of double stranded DNA antibody. The increase in FRET signal over time means that formation of LSD1-nucleosome complexes is taking place.

Figure 3:
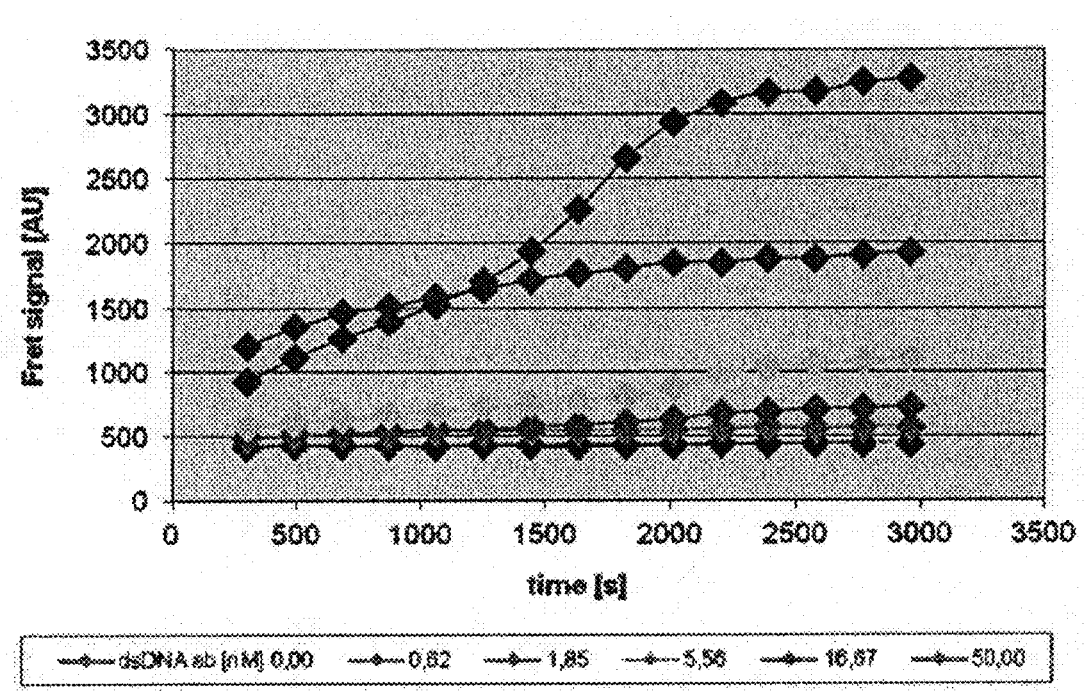

FIG. 3. FRET signal over time at 2.22 nm nucleosome concentration, 16 nm GST-Tb antibody, 7 nm LSD1 and increasing concentrations of histone H2B antibody. The increase in FRET signal over time means that formation of LSD1-nucleosome complexes is taking place.

Figure 4A:
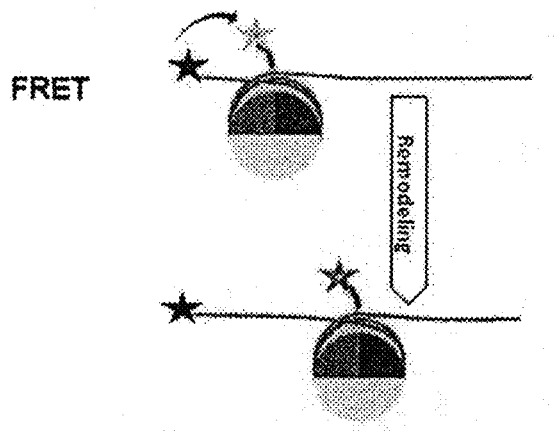

FIG. 4A: Nucleosome sliding by the ACF remodeling complex.

The labeled nucleosome and labeled DNA are in close proximity with shows FRET. When the nucleosome slides along the DNA the distance between donor and acceptor increases and the FRET signal is lost.

Figure 4B:
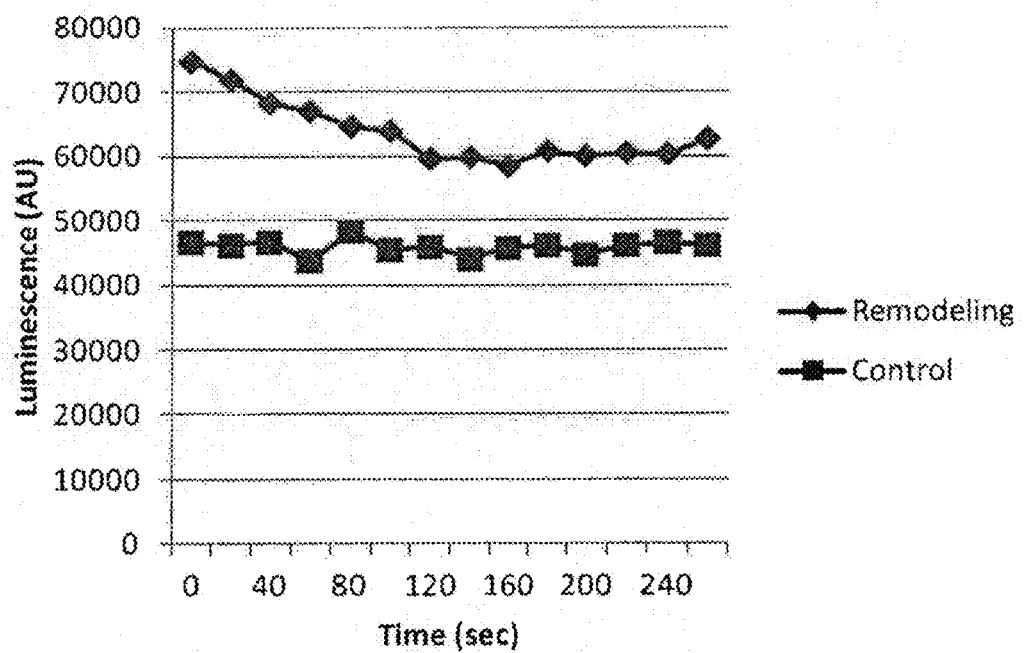

FIG. 4B: Results from sliding assay.

Nucleosome on the remodeling DNA template shows FRET signal, which is reduced over time by the remodeling complex. The nucleosome on the control DNA shows little FRET and remodeling cannot lower the signal any further.

Figure 5:
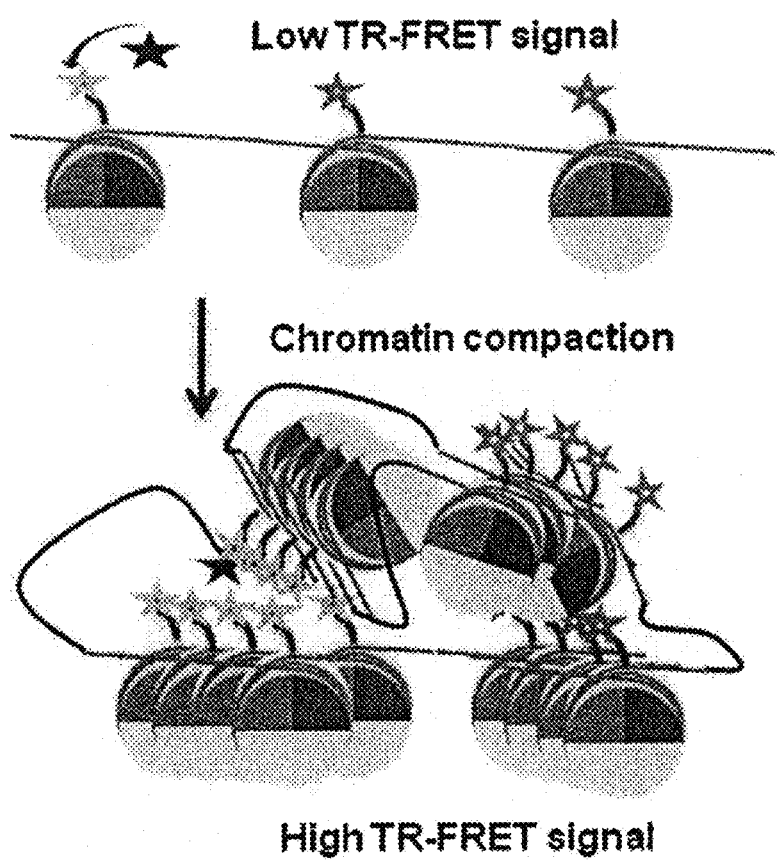

FIG. 5: Compacting assay by utilizing intramolecular FRET. Compacting of the chromatin will bring more FRET acceptor molecules in close proximity to the donor, thereby increasing the FRET signal.

Figure 6:
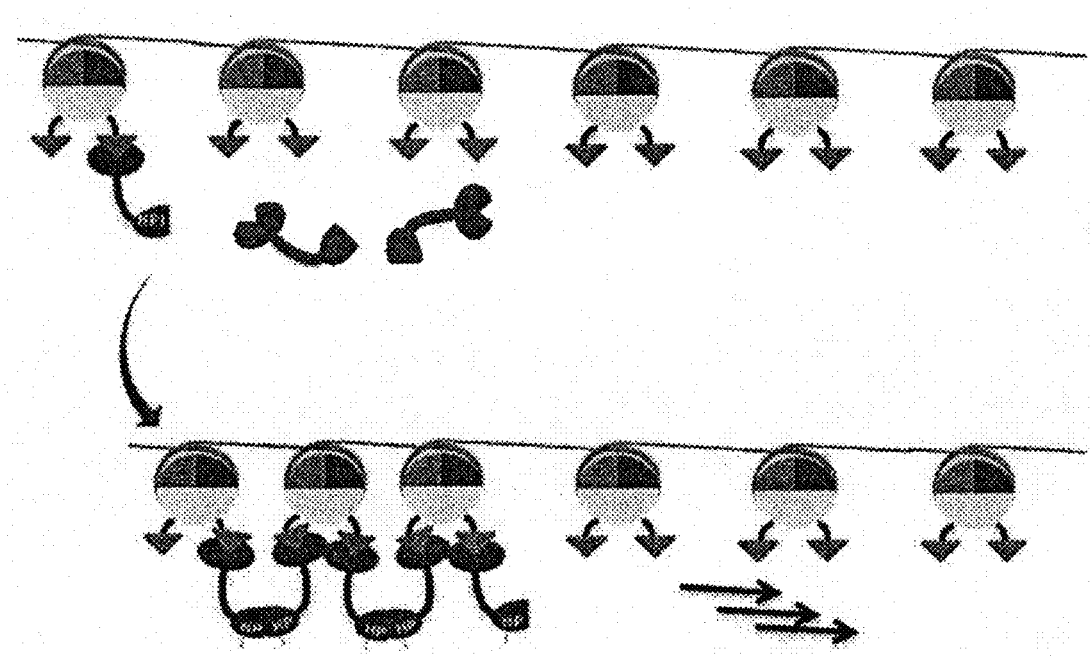

FIG. 6: Compacting of the chromatin by HP1.

HP1 binds to methylated H3. HP1 that is bound to histones dimerizes and compacts the chromatin.

DETAILED DESCRIPTION OF THE INVENTION

Where the term "comprise" or "comprising" is used in the present description and claims, it does not exclude other elements or steps. For the purposes of the present invention, the term "consisting of" is considered to be an optional embodiment of the term "comprising of". If hereinafter a group is defined to comprise at least a certain number of embodiments, this is also to be understood to disclose a group which optionally consists only of these embodiments.

Where an indefinite or a definite article is used when referring to a singular noun e.g. "a" or "an", "the", this includes a plural form of that noun unless specifically stated.

In the context of the present invention any numerical value indicated is typically associated with an interval of accuracy that the person skilled in the art will understand to still ensure the technical effect of the feature in question. As used herein, the deviation from the indicated numerical value is in the range of ±10%, and preferably of ±5%. The aforementioned deviation from the indicated numerical interval of ±10%, and preferably of ±5% is also indicated by the terms "about" and "approximately" used herein with respect to a numerical value.

One aspect of the invention refers to a method for determining a binding and/or functional interaction of a protein of interest with a nucleosomal substrate comprising DNA wrapped around histone octamers, wherein the method comprises the following steps:

(a) forming a composition of matter comprising the protein of interest and the nucleosomal substrate;

(b) determining a value indicative for the binding and/or functional interaction of the protein of interest with the nucleosomal substrate;

wherein at least one histone type of the nucleosomal substrate has a homogenous post-translational modification pattern.

The term "protein of interest" includes proteins that may interact with the nucleosomal substrate. The term also includes modified, truncated and synthetic proteins and peptides as well as wild-type proteins and peptides. Typically, the protein of interest is a post-translational modifier, such as post-translational modifying enzymes, e.g. acetyl-transferases (HATs), histon deacetylases (HDACs), histone methyl transferases (HMTs), histone demethylases (HDMs) histone kinases (HPT), Histone Phosphatases (HPPT), histone ubiquitin ligases (E3) and de-ubiquitinases (DUBs).

A further aspect of the invention relates to a method for determining the compaction state of a nucleosomal substrate comprising DNA wrapped around histone octamers, wherein the method comprises the following steps:

(a) providing the nucleosomal substrate which is labeled by both a FRET donor and a FRET acceptor;

(b) determining a value indicative for the compaction state of a nucleosomal substrate by FRET detection;

wherein at least one histone type of the nucleosomal substrate has a homogenous post-translational modification pattern.

The term "nucleosomal substrate" includes mononucleosomes and oligonucleosomes. Mononucleosomes are composed of histone octamers that are wrapped by DNA. Histone octamers may consist of two copies of each of the four core histone proteins (H2A, H2B, H3 and H4). However histone octamers may also contain a different combination of histones and histone variants. Typically, a histone octamer is wrapped by double-stranded DNA. The double-stranded DNA may have a length of 140 bp to 210 bp, typically of 147 bp to 201 bp, such as 187 bp. Oligonucleosomes contain more than one mononucleosome, such as 2, 3, 4, 5, 6, 7, 8, 9, 10, 11, 12, 13, 14, 15, 16, 17, 18, 19 or more mononucleosomes. Usually, in oligonucleosomes, the mononucleosomes (e.g. histone octamers wrapped by 187 bp DNA) are connected in series. Usually, the histones are connected by linker DNA of about 1 bp to 100 bp, 10 bp to 50 bp such as 23 bp. Typically, an oligonucleosome may comprise 12 mononucleosomes. The mono- or oligonucleosomes may comprise further proteins, such as linker histones like histone H1 or H5 or natural or non-naturals variant thereof.

Nucleosomes obtained from natural sources have a heterogeneous modification pattern. That means that in a population of the one histone type, for example histones of the type H2B, the individual histones may differ in their modifications at a specific site or at multiple sites of the sequence.

The posttranslational modification pattern is defined by the presence or absence of certain post-translational modification groups such as acetyl-, citrullyl, methyl-, phosphoryl-, propionyl-, ADP-ribosyl or ubiquitinyl moieties at certain amino acids positions of the histone. An amino acid may have several modification states. For example, the amino acid lysine may exist in mono-, di- or trimethylated state or the amino acid arginine may be methylated once or twice.

By the term "homogenous modification pattern" it is meant that in a population of one histone type at least 80%, at least 90%, at least 95%, 98% or 99%, 99.5%, 99.9% or 100% of the histones have the identical homogeneous post-translational modification patterns at a specific site of the sequence. The proportion of histones having a homogenous modification pattern in a population may be measured by mass-spectrometry, such as peptide mass fingerprinting (PMF) or liquid chromatography electron spray ionization mass spectrometry (LC-ESI-MS).

The site of the sequence or sequence region may range from a single position to the full length histone. The site of the sequence or sequence region may contain the N-terminal histone tail, the C-terminal histone tail or both histone tails. In specific embodiments, the sequence segment contains the N-terminal histone tail or the C-terminal histone tail.

At least one histone type of the nucleosomal substrate may have a homogenous post-translational modification pattern. That means that one, two, three of four histone types of the histone octamers may have a post-translational modification pattern. In specific embodiments, one histone type of the histone octamers may have a homogenous post-translational modification pattern.

The term "histone type" means one of the four histone proteins that build the histone octamer. Exemplary histone proteins are H2A, H2B, H3 or H4 or natural or non-natural variants thereof. Usually a histone octamers may be composed of the four histone types H2A, H2B, H3 or H4.

With the term "natural variant" as used herein, natural occurring sequence variants of the protein of the same gene family are meant. A natural variant of histone H3 is for example CENPA. A natural variant of H2A is for example macroH2A.

A "non-natural variant" or also "variant" of a protein may be any truncated, elongated and/or permutated form of the protein which is not known to be a natural variant of the protein.

In one embodiment, the histone type of the nucleosomal substrate having a homogenous post-translational modification pattern is histone H3 which is trimethylated at lysine residue 36 (H3K36me3).

The nucleosomal substrate may comprise mononucleosomes or oligonucleosomes or a mixture thereof.

In the step of forming a composition of matter comprising the protein of interest and the nucleosomal substrate, the protein of interest and the nucleosomal substrate and optionally further compounds are brought into contact with each other. Optionally, the composition of matter may be mixed, for example by pipetting the composition of matter and/or spinning the well plate comprising the composition of matter. In particular, when the assay employs detecting a fluorescence signal, reporter dyes may be added to the solution, for example when the nucleosomal substrate and/or the protein of interest are not covalently labeled.

The term "value indicative for the binding and/or functional interaction of the protein of interest with the nucleosomal substrate" is to be understood as a value that is indicative for the binding affinity such as Kd, binding kinetic parameters such as $K_{on}$, $K_{off}$, residence time, kinetic selectivity, binding thermodynamics such as enthalpy and entropy or the function of a protein of interest with relation to the nucleosomal substrate, i.e. its mechanistic role. The value that is indicative for the function of a protein of interest with relation to the nucleosomal substrate may be a value indicating the compaction state of the chromatin and/or the presence or absence of modification on histone or DNA molecules.

In one embodiment, the value indicative for the binding and/or functional interaction may be determined by optical detection, optionally fluorescent detection.

In a specific embodiment, the fluorescent detection is FRET detection, optionally TR-FRET detection. FRET (fluorescence resonance energy transfer) is based on the transfer of energy between two fluorophores, i.e. a donor and an acceptor, when these fluorophores are in close proximity. When the two fluorophores come close enough to each other, excitation of the donor by an energy source triggers an energy transfer towards the acceptor, which in turn emits specific fluorescence at a given wavelength.

In a FRET assay measuring the compaction state of the chromatin, the acceptor and donor molecules may be located only on the DNA molecule, or only on the histone proteins or both on DNA and on histone proteins. Optionally, the acceptor and donor molecules may be located only the DNA molecule. The acceptor and donor molecules may be located on the opposite ends of the DNA molecule.

In a preferred embodiment both acceptor and donor molecules are located on the nucleosomal substrate. The donor molecule may be located at the DNA and the acceptor molecule may be located at the histone. Alternatively the acceptor molecule may be located at the DNA and the donor molecule may be located at the histone.

In a particularly preferred embodiment the donor molecule is located at the DNA and the acceptor molecule is located at the histone.

In a specific embodiment several nucleosomes of an oligonucleosomes are labeled.

With Fluorescent Resonance Energy Transfer (FRET) is possible to show that two molecules or parts of the same molecule are in close proximity (up to 10 nm). A donor molecule is excited with light at a wavelength at the peak of its excitation spectrum. In the normal circumstance the donor would return to its relaxed state by emitting light from its emission spectrum. When an appropriate acceptor molecule is in close proximity of the donor in its excited state, the energy can be transferred to the acceptor molecule, which in turn relaxes by emitting light from its emission spectrum. Using a filter which only allows light of the acceptor wavelength to pass through, the FRET signal can be quantified. By measuring in a continuous mode, changes to a system can be observed by increase or decrease of the FRET signal.

The FRET measurement may be repeated. For example at least 2 cycles, at least 5 cycles, at least 10 cycles such as 15 cycles or more are carried out. The interval between the cycles may be for example 30 s, 1 min, 2 min, 3 min, 4 min or 5 min.

TR-FRET (time resolved FRET) combines FRET technology with time-resolved measurement of fluorescence, eliminating short-lived background fluorescence. The introduction of a time delay between the excitation and the fluorescence measurement allows the signal to be cleared of non-specific short-lived emissions.

The time delay may be for example from between 30 µs to 300 µs, e.g. between 50 µs to 150 µs.

The TR-FRET measurement may be repeated. For example at least 2 cycles, at least 5 cycles, at least 10 cycles such as 15 cycles or more are carried out. The interval between the cycles may be for example 30 s, 1 min, 2 min, 3 min, 4 min or 5 min.

In a specific embodiment of FRET detection, Terbium (Tb) or Europium (Eu) and a far red dye (such as Dylight 650 from Thermo Scientific, Alexa Fluor 647 form abeam, Alexa Fluor 660 from abcam, Atto 633 from ATTO-TEC, Atto 647 from ATTO-TEC, Atto 647N from ATTO-TEC, d2 from sigma-aldrich, DY-630 from dyomics, DY 635 from dyomics, DY 680 from dyomics, Dylight 649 from Thermo Scientific, TYE 665 from exicon, XL665 from cisbio, Cy5 from GE healthcare lifesciences) are combined.

In a more specific embodiment of FRET detection, Tb and a far red dye with excitation maximum at 652 nm and emission maximum at 672 nm (Dylight 650) are combined.

In another specific embodiment the donor molecule Atto 550 from ATTO-TEC and the acceptor molecule Atto 647N from ATTO-TEC are combined.

Properties of Dylight 650 are as follows:

| | |
|---|---|
| Excitation/emission maxima | 652 nm/672 nm |
| Emission color | Far Red |
| Molar extinction coefficient ($\epsilon$) | 250,000 M-1 cm-1 |
| Correction factor (A280/A652) | 0.037 |
| Molecular weight | NHS ester: 1066 g/mol |
| | Maleimide: 1091 g/mol |

In a specific embodiment of TR-FRET detection, Terbium (Tb) or Europium (Eu) and a far red dye (such as Dylight 650, Alexa Fluor 647, Cy5) are combined.

In a more specific embodiment of TR-FRET detection, Tb or Eu and a far red dye with excitation maximum at 652 nm and emission maximum at 672 nm (Dylight 650) are combined.

When using the combination of Tb or Eu and the far red dye (Dylight 650), fluorescence at 620 nm and 655 nm may be measured. It has been found that the measurement of Tb and the far red dye such as Dylight 650 leads to good sensitivity of TR-FRET detection assay.

The measurement of the fluorescent signal, for example the FRET signal, may be carried out with standard fluorescent imaging microscopes or fluorescent imaging plate readers, such as the PHERAstar microplate reader (BMG Labtech), Artemis TR-FRET (Cosmo Bio), HTS 7000 (Perkin Elmer) or SpectraMax M5 (Molecular Devices). Usually, the PHERAstar microplate reader (BMG Labtech) is used.

The excitation of the fluorescent molecule may occur in a range of 320 nm to 370 nm, such as 330 nm to 350 nm, for example at 360 nm.

In another embodiment the excitation of the fluorescent molecule may occur in a range of 520 nm to 570 nm, such as 530 nm to 550 nm, for example at 540 nm.

The emitted signal may be detected in a range of 580 to 640, 610 nm to 630 nm and in a range of 650 nm to 690 nm, such as 660nm to 680nm, for example at 665 nm or at 672 nm or for exampled at 590 and 680.

The fluorescent label may be attached to different molecules, such as peptides, proteins and nucleic acids.

The fluorescent label may be covalently bound to the protein of interest. Alternatively, the fluorescent label may be covalently bound to an antibody which binds specifically to the protein of interest to be labeled. Alternatively, the fluorescent label may be covalently bound to an affinity tag binding protein or antibody that binds the corresponding affinity tag, such as a GST, his, FLAG, digoxigenin, streptavidin or c-myc, which is bound to the protein of interest. Typically, a GST-tag may be bound to the protein of interest. In particular, the GST-tag may be bound to a post-translational modifier.

The nucleosomal substrate may be labeled with a fluorescent label. To this end, the DNA and/or the histones may be labeled with a fluorescent label. The fluorescent label may be covalently attached to an antibody specifically binding DNA, such as double stranded DNA or to histone proteins. The fluorescent label may be attached to a binding protein or fragment thereof such as a binding domain which specifically binds DNA, such as double stranded DNA or to histone proteins. Alternatively, the fluorescent label may be attached to the DNA and/or the histone. Typically, the fluorescent label will be attached to the peptide having a homogenous post-translational modification pattern.

The donor and the acceptor may be attached to different molecules, such as peptides, proteins and nucleic acids. The FRET label may be attached to the protein of interest. Alternatively, the FRET label may be attached to an antibody which binds specifically to the protein of interest to be labeled. Alternatively, the FRET label may be attached to an affinity tag binding protein or antibody that binds the corresponding affinity tag, such as a GST, his, FLAG, digoxigenin, streptavidin or c-myc which is linked to the protein of interest. Typically, a GST-tag may be bound to the protein of interest. In particular, the GST-tag may be bound to a post-translational modifier.

In an exemplary embodiment, the nucleosomal substrate is labeled either with an FRET donor or a FRET acceptor. In particular, the nucleosomal substrate may be labeled with a TR-FRET donor or a TR-FRET acceptor. To this end, the DNA and/or the histones may be labeled with a FRET donor or a FRET acceptor. The FRET label may be attached to an antibody specifically binding DNA, such as double stranded DNA or to histone proteins. The FRET label may be attached to a binding protein or fragment thereof such as a binding domain which specifically binds DNA, such as double stranded DNA or to histone proteins. Alternatively, the FRET label may be attached to the DNA and/or the histone. Typically, the FRET label will be attached to the peptide having a homogenous post-translational modification pattern.

In a further embodiment, the protein of interest is labeled either with a FRET donor or a FRET acceptor. In particular, the protein of interest may be labeled with a TR-FRET donor or a TR-FRET acceptor.

A "TR-FRET donor" as used herein is a fluorescent molecule that when excited the emission of the light from the molecule occurs with a time delay after excitation, for example a time delay in a range of 30 µs to 150 µs, typically in a range of 50 µs to 100 µs, for example of 60 µs or 65 µs. A "TR-FRET acceptor" as used herein is a fluorescent molecule that can be excited by the emission of the TR-FRET donor used in the assay.

In another embodiment the post-translational modifier may be labeled with a TR-FRET donor or a TR-FRET acceptor.

In a more specific embodiment, the nucleosomal substrate and the protein of interest are labeled with corresponding FRET reporter dye molecules, optionally by compatible TR-FRET reporter dye molecules. That means, if the nucleosomal substrate is labeled with the FRET donor the protein of interest may be labeled with a corresponding FRET acceptor. Vice versa, the nucleosomal substrate may be labeled with a FRET acceptor and the protein of interest may be labeled with a corresponding FRET donor.

In particular, the nucleosomal substrate may be labeled with Tb or Eu and the protein of interest may be labeled with a far red dye such as Dylight 650. Alternatively, the nucleosomal substrate may be may be labeled with a far red dye such as Dylight 650 and the protein of interest may be labeled with Tb or Eu.

In another embodiment, the nucleosomal substrate may be labeled with Atto 647N and the protein of interest may be labeled with Atto 550. Alternatively, the nucleosomal substrate may be labeled with Atto 550 and the protein of interest may be labeled with Atto 647N.

In a further embodiment, the nucleosomal substrate may be labeled with Tb or Eu and the post-translational modifier may be labeled with a far red dye such as Dylight 650. Alternatively, the nucleosomal substrate may be may be labeled with a far red dye such as Dylight 650 and the post-translational modifier may be labeled with Tb or Eu.

In another embodiment, the nucleosomal substrate may be labeled with Atto 647N and the post-translational modifier may be labeled with Atto 550. Alternatively, the nucleosomal substrate may be labeled with Atto 550 and the post-translational modifier may be labeled with Atto 647N.

In particular, the nucleosomal substrate may be labeled with Tb or Eu and the protein of interest may be labeled with a far red dye such as Dylight 650 using the TR-FRET assay detecting emission in a range of 610 nm to 630 nm and in a range of 650 nm to 690 nm, such as in a range of 660 nm to 680 nm, for example about 665 nm or about 672 nm. Alternatively, the nucleosomal substrate may be may be labeled with a far red dye such as Dylight 650 and the protein of interest may be labeled with Tb or Eu using the TR-FRET assay detecting emission at about 620 nm and about 665 nm.

In an exemplary embodiment, the nucleosomal substrate may be labeled with Tb and the post-translational modifier may be labeled with a far red dye such as Dylight 650 using the TR-FRET assay detecting emission at 610 nm to 630 nm and in a range of 650 nm to 690 nm, such as in a range of 660 nm to 680 nm, for example about 665 nm or about 672 nm. Alternatively, the nucleosomal substrate may be may be labeled with a far red dye such as Dylight 650 and the post-translational modifier may be labeled with Tb using the TR-FRET assay detecting emission at about 620 nm and about 665 nm.

In particular, the nucleosomal substrate may be labeled with Tb or Eu and the protein of interest may be labeled with a far red dye such as Dylight 650 using the TR-FRET assay detecting emission at about 620 nm and about 665 nm. Alternatively, the nucleosomal substrate may be may be labeled with a far red dye such as Dylight 650 and the protein of interest may be labeled with Tb or Eu using the TR-FRET assay detecting emission at about 620 nm and about 665 nm.

In an exemplary embodiment, the nucleosomal substrate may be labeled with Tb and the post-translational modifier may be labeled with a far red dye such as Dylight 650 using the TR-FRET assay detecting emission at 620 nm and 665nm. Alternatively, the nucleosomal substrate may be labeled with a far red dye such as Dylight 650 and the post-translational modifier may be labeled with Tb using the TR-FRET assay detecting emission at 620 nm and 665nm.

In a specific embodiment, the value indicative for the binding and/or functional interaction depends on the compaction state of the nucleosomal substrate. The value indicating the compaction state of the chromatin may be for example measured in a FRET assay in which both acceptor and donor molecules located on the nucleosomal substrate. Acceptor and donor molecules may be arranged such that in a certain chromatin state (for example relaxed state) both molecules are remote from each other so that no energy transfer occurs while in a second chromatin state (for example compacted stated) donor and acceptor come close enough that that energy transfer occurs.

The terms "compaction state of the nucleosomal substrate" and "chromatin compaction" are used herein interchangeable.

One embodiment of the invention relates to a method for determining a binding and/or functional interaction of a protein of interest with a nucleosomal substrate comprising DNA wrapped around histone octamers, wherein the method comprises the following steps:

(a) forming a composition of matter comprising the protein of interest and the nucleosomal substrate;

(b) determining a value indicative for the binding and/or functional interaction of the protein of interest with the nucleosomal substrate;

wherein at least one histone type of the nucleosomal substrate has a homogenous post-translational modification pattern;

wherein the value indicative for the binding and/or functional interaction depends on the compaction state of the nucleosomal substrate.

One embodiment of the invention relates to a method for determining a binding and/or functional interaction of a protein of interest with a nucleosomal substrate comprising DNA wrapped around histone octamers, wherein the method comprises the following steps:

(a) forming a composition of matter comprising the protein of interest and the nucleosomal substrate;

(b) determining a value indicative for the binding and/or functional interaction of the protein of interest with the nucleosomal substrate;

wherein at least one histone type of the nucleosomal substrate has a homogenous post-translational modification pattern;

wherein the value indicative for the binding and/or functional interaction depends on the compaction state of the nucleosomal substrate, wherein the DNA wrapped around histone octamers is arranged in oligonucleosomes.

Another specific embodiment refers to a method for determining a binding and/or functional interaction of a protein of interest with a nucleosomal substrate comprising DNA wrapped around histone octamers, wherein the method comprises the following steps:

(a) forming a composition of matter comprising the protein of interest and the nucleosomal substrate;

(b) determining a value indicative for the binding and/or functional interaction of the protein of interest with the nucleosomal substrate;

wherein at least one histone type of the nucleosomal substrate has a homogenous post-translational modification pattern;

wherein the value indicative for the binding and/or functional interaction depends on the compaction state of the nucleosomal substrate, wherein both FRET acceptor and FRET donor are located on the nucleosomal substrate.

Another specific embodiment refers to a method for determining a binding and/or functional interaction of a protein of interest with a nucleosomal substrate comprising DNA wrapped around histone octamers, wherein the method comprises the following steps:

(a) forming a composition of matter comprising the protein of interest and the nucleosomal substrate;

(b) determining a value indicative for the binding and/or functional interaction of the protein of interest with the nucleosomal substrate;

wherein at least one histone type of the nucleosomal substrate has a homogenous post-translational modification pattern;

wherein the value indicative for the binding and/or functional interaction depends on the compaction state of the nucleosomal substrate, wherein both FRET acceptor and FRET donor are located on the nucleosomal substrate, wherein the DNA wrapped around histone octamers is arranged in oligonucleosomes.

Another embodiment of the invention relates to a method for determining a binding and/or functional interaction of a protein of interest with a nucleosomal substrate comprising DNA wrapped around histone octamers, wherein the method comprises the following steps:

(a) forming a composition of matter comprising the protein of interest and the nucleosomal substrate;

(b) determining a value indicative for the binding and/or functional interaction of the protein of interest with the nucleosomal substrate;

wherein at least one histone type of the nucleosomal substrate has a homogenous post-translational modification pattern;

wherein the value indicative for the binding and/or functional interaction depends on the compaction state of the nucleosomal substrate, wherein the FRET donor is located at the DNA and the FRET acceptor is located at the histone.

A specific embodiment of the invention relates to a method for determining a binding and/or functional interaction of a protein of interest with a nucleosomal substrate comprising DNA wrapped around histone octamers, wherein the method comprises the following steps:

(a) forming a composition of matter comprising the protein of interest and the nucleosomal substrate;

(b) determining a value indicative for the binding and/or functional interaction of the protein of interest with the nucleosomal substrate;

wherein at least one histone type of the nucleosomal substrate has a homogenous post-translational modification pattern;

wherein the value indicative for the binding and/or functional interaction depends on the compaction state of the nucleosomal substrate, wherein the DNA wrapped around histone octamers is arranged in oligonucleosomes, wherein the FRET donor is located at the DNA and the FRET acceptor is located at the histone and wherein several nucleosomes of the oligonucleosomes are labeled.

In another embodiment, the composition of matter further comprises a molecule which is a candidate for modulating the binding and/or functional interaction of the protein of interest with the nucleosomal substrate.

The candidate for modulating the binding and/or functional interaction of the protein of interest with the nucleosomal substrate may be any drug, such as small molecules, peptide, protein, nucleic acid, such as ribonucleic acid or deoxyribonucleic acid.

This assay allows to measure the residence time of the drug candidate. By following the emergence of the TR-FRET signal over a period of time, typically up to 6 hours, the drug-target residence time can be calculated by fitting monoexponential decay functions to the displacement curves.

In a specific embodiment, each of the histone types has a homogenous post-translational modification pattern.

In a further embodiment, method is carried out in medium to high through-put format, optionally in high through-put format. The method may be carried out in 96, 384 or 1536 well plates. Alternatively, the method may be carried out in microarrays in which the nucleosomal substrate is attached to a surface.

In another embodiment, the composition of matter further comprises a reporter protein capable of recognizing a histone having a post-translational modification. In this embodiment the protein of interest, e.g. the post-transla- tional modifier may not be labeled. Using permissive assay conditions the post-translational modifier may remove or add specific post-translational modifications from or to the nucleosomal substrate based on its intrinsic substrate specificity. The reporter protein directed against specific post-translational modifications may be labeled with a FRET reporter dye. Upon binding of the reporter protein to the specific site of modification, the FRET reporter on the reporter protein comes into close proximity with the corresponding FRET reporter dyes on the nucleosomal substrate and a FRET signal is generated.

The reporter protein may be an antibody or a histone binding protein or fragments thereof or mutants thereof capable of binding to specific post-translational modification on the histone tails, such as histone binding domains.

In one embodiment the histone binding protein may be a histone binding domain or a protein containing a histone binding domain. The histone binding domain may contain for example BROMO-, CHROMO- and/or PHD finger domains.

The histone binding proteins include enzymes and chromatin remodeling factors, such as MLL1/2, MLL3/4, SMYD3, USP22, G9A, HP1, JMJD2a, JMJD2c, BRD4, SMARCA2, p300, EZH2, JARID1a, JARID1b, SetD8, PADI4, PHF8, PRMT5, SetDB8, NSD1, NSD2, NSD3, FBXL10, JMJD3, Dot1L, LSD1, HDAC1-11, Sirtuin 1-7, Tip60, PCAF, UTX, EZH1, PRMT3, PRMT4, USP16.

In a preferred embodiment the histone binding protein may be selected from the group comprising, preferably consisting of EZH2, SMYD3, JMJD3, BRD4, NSD2, LSD1, HDAC2 and HDAC6.

The reporter protein may be labeled, optionally fluorescently labeled. Typically, the reporter protein and the nucleosomal substrate are labeled by corresponding FRET reporter dye molecules, optionally by compatible TR-FRET reporter dye molecules.

In an alternative embodiment, the value indicative for the binding and/or functional interaction is determined by surface plasma resonance spectroscopy.

Another aspect of the invention is a method for providing a nucleosomal substrate comprising DNA wrapped around histone octamers, wherein the method comprises the following steps:

(a) providing histone octamers wherein at least one of the histone types of the histone octamer has a homogenous post-translational modification pattern;

(b) combining DNA with the histone octamers thereby obtaining the nucleosomal substrate.

The nucleosomal substrate may be provided in labeled or unlabeled form. In a specific embodiment, the nucleosomal substrate is labeled with a fluorescent label. Usually, either the DNA is labeled and/or at least one of the histone types is labeled. The DNA may be labeled in a PCR reaction or by ligation of labeled oligonucleotides. DNA may be labeled at the 5'-end or at the 3'-end, preferably at the 5'-end. The histone may be covalently labeled with the fluorescent dye, for example via attachment of the dye to the peptide having the post-translational modification pattern during peptide synthesis.

The at least one histone type having a homogenous post-translational modification pattern may be provided by total chemical synthesis. Methods for total chemical synthesis are well known in the art to the skilled person. Total chemical synthesis of proteins is for exampled described in Sato, K., Angew. Chem. Int. Ed. Engl. 2013, (30):7855-9.

In another embodiment, the at least one histone type having a homogenous post-translational modification pattern is provided by site-specific incorporation of a amino acid analogue, optionally site-specific incorporation of a methyl and/or acetyl-lysine analogue, typically of a methyl lysine analogue.

Typically, the at least one histone type having a homogenous post-translational modification pattern is provided by the method comprising the following the steps:

(i) providing truncated histones of a histone type;

(ii) providing peptides having a homogenous post-translational modification pattern;

(iii) ligating the truncated histones of step (i) and the peptides of step (ii).

A "truncated histone" refers to a histone that has a shorter sequence than its wild-type full-length form. That means that the sequence of the truncated histone corresponds to a sequence of the full-length histone minus a sequence region that is omitted. The sequence region to be omitted may comprise of several parts distributed over the full-length sequence of the histone. Usually, the N-terminal and/or the C-terminal region of the histone is truncated. Typically, either the N-terminal or the C-terminal region of the histone is truncated. Usually, the sequence region that is omitted has a length in the range of 1 amino acids (aa) to 100 aa, of 3 aa to 40 aa, of 5 aa to 30 aa, of 10 aa to 25 aa.

The truncated histone may be provided by expression, for example by expression in *E.coli*, yeast, insect or mammal cells. Typically, the truncated histone is provided by expression in *E.coli*. Alternatively the truncated histone may be provided by chemical synthesis. When providing the truncated histone by chemical synthesis, several segments of the truncated histone may be chemically synthesized and then ligated to obtain the truncated histone.

Usually, the peptide having a homogenous post-translational modification corresponds to the sequence that is omitted in the truncated protein. For example, the sequence of the peptide is the sequence of the full-length histone minus the sequence of the truncated histone, including variants thereof, such as truncated, prolonged and/or mutated variants.

The ligating step may be a native chemical ligation reaction.

The ligation may occur in the presence of a catalyst, such as benzylmercaptane, benzenthiol, thiophenol or mercaptophenyl acetic acid. It was found that the yield of the native chemical ligation may be improved by the use of mercaptophenyl acetic acid (MPAA). Thus, in the ligating step, MPAA may be added.

Further, it was found that the yield of the ligation reaction could be improved by the use of a ligation buffer essentially without dissolved oxygen. Herein, without dissolved oxygen includes a reduction of the dissolved oxygen at least by several orders of magnitude.

Typically, the ligation buffer is prepared by mixing the buffer components followed by degassing. Usually, the degassing step comprises applying helium through a needle into the buffer solution and stirring the solution. The solution may be stirred with a magnetic stir bar. A layer of argon maybe applied on the buffer.

The truncated histone and the peptide corresponding to the truncated region of the truncated histone may be mixed at a molar ratio of from 1:5 to 1:1.1, such as from 1:3 to 1:1. Typically the truncated histone and the peptide corresponding to the truncated region of the truncated histone may be mixed at a molar ratio of 1:1.3.

Further, after the mixing of the truncated histone with the synthetic peptide the readjustment of the buffer to a pH in the range of from pH 6.8 to pH 7.2, from pH 7 to pH 7.1 such as a pH of 7.05 may improve the yield of the ligation reaction. Typically, after mixing the truncated histone with the synthetic peptide, the pH of the ligating buffer readjusted to pH 7.05.

The ligation may yield at least more than 40%, at least more than 45%, at least more than 50%, at least more than 55%, at least more than 60%, at least more than 70%, at least more than 80% or at least more than 90% of ligated histone product. Typically, the ligation may yield at least more than 50% ligated histone product.

In another embodiment, the histones having a homogenous post-translational modification pattern, may be provided by site-specific incorporation of a amino acid analogue, optionally site-specific incorporation of a methyl and/or acetyl-lysine analogue, as for example described in Guo, 2008 (Angew. Che., Int. Ed., 47, 6399-6401). This method may also be used for the provision of full-length histones or for the provision of truncated histones and then be combined with the native chemical ligation of a peptide having a homologous post-translational modification pattern.

The peptide having the post-translational modification pattern may be produced by chemical synthesis.

In a specific embodiment the peptide having the homogenous post-translational modification pattern may be produced by native chemical ligation.

Native chemical ligation reaction is a chemo selective peptide bound forming process. It may be carried out in either solution or on the solid phase.

In a specific embodiment the peptide having the post-translational modification was synthesized by Fmoc/But strategy developed by Sheppard (E. Atherton and R. C. Sheppard in S. Udenfriend and J. Mcienhofer, The Peptides: Analysis, Synthesis, Biology, Acadeic Press, New York, 1987). A bis(2-SulfanylEthyl)Amino-trityl-polystere (SEA-PS) resin may be used for the peptide synthesis. This method allows to incorporate the post-translational modification of interest at the desired position. Optionally, nucleosomes with fluorescent dyes may be incorporated by solid phase peptide synthesis.

In an exemplary embodiment, the peptide comprises permutations that improve the ligation reaction. By using the SEA peptides (Dheurj. et al. J.Org. Chem. 2011, 76: 3194-3202) rather than conventional benzene-thioester based peptides, yields of the ligation reactions and homogeneity of the final ligated product could be improved dramatically. There may be a lower chance that the final histone product is contaminated with unligated truncated histone because the yield of the ligated product may be higher.

The histone may comprise an affinity tag and/or ,a. fluorescent tag. In particular, the, truncated histone may comprise an affinity tag and/or a fluorescent tag.

The truncated histone may be truncated at the C-terminus and the peptide comprises the C-terminus of the protein. Alternatively, the truncated histone may be truncated at the N-terminus and the peptide comprises the N-terminus of the histone.

Another aspect of the invention relates to a nucleosomal substrate comprising DNA wrapped around histone octamers, wherein at least one of the histone types of the nucleosomal substrate has a homogenous post-translational modification pattern, wherein the nucleosomal substrate is labeled.

At least of the histone types of the nucleosomal substrate has a homogenous post-translational modification pattern. That means that one, two, three or all four histones each have a homogenous post-translational modification pattern.

In particular, one histone type has a homogenous post-translational modification pattern.

The DNA sequence wrapped around the histone octamers in the nucleosomal substrate may be predetermined. Usually, a nucleosome positioning sequence is used. A nucleosome positioning sequence is a defined DNA sequence that has a high affinity for the histone octamer. The nucleosome positioning sequence may be natural, such as Lytechinus variegatus fragment from the 5S ribosomal RNA (SEQ ID NO: 2) or non-natural, such as nucleosome positioning sequence "601" (SEQ ID NO: 1). Typically, the non-natural nucleosome positioning sequence "601" is used.

```
601, 201 bp, (SEQ ID NO.: 1):
CCTGGAGAATCCCGGTGCCGAGGCCGCTCAATTGGTCGTAGCAAGCTCTA

GCACCGCTTAAACGCACGTACGCGCTGTCCCCCGCGTTTTAACCGCCAAG

GGGATTACTCCCTAGTCTCCAGGCACGTGTCAGATATATACATCCTGTGC

ATGTATTGAACAGCGACTCGGGTTATGTGATGGACCCTATACGCGGCCGC

C 5S, 209 bp, (SEQ ID NO.: 2):
GGAATTCCAACGAATAACTTCCAGGGATTTATAAGCCGATGACGTCATAA

CATCCCTGACCCTTTAAATAGCTTAACTTTCATCAAGCAAGAGCCTACGA

CCATACCATGCTGAATATACCGGTTCTCGTCCGATCACCGAAGTCAAGCA

GCATAGGGCTCGGTTAGTACTTGGATGGGAGACCGCCTGGGAATACCGA

ATTCCCCGAG
```

In the nucleosomal substrate, the DNA wrapped around histone octamers can be arranged in mononucleosomes and/or oligonucleosomes.

The nucleosomal substrate can be labeled. In particular, the nucleosomal substrate may be fluorescently labeled.

In a specific embodiment the method for determining a binding and/or functional interaction comprises the following steps:

(a) forming a composition of matter comprising the protein of interest and the nucleosomal substrate;

(b) determining a value indicative for the binding and/or functional interaction of the protein of interest with the nucleosomal substrate;

wherein at least one of the histone types of the nucleosomal substrate has a homogenous post-translational modification pattern;

wherein the value indicative for the binding and/or functional interaction is determined by FRET detection.

In another embodiment the method for determining a binding and/or functional interaction comprises the following steps:

(a) forming a composition of matter comprising the protein of interest and the nucleosomal substrate;

(b) determining a value indicative for the binding and/or functional interaction of the protein of interest with the nucleosomal substrate;

wherein at least one of the histone types of the nucleosomal substrate has a homogenous post-translational modification pattern;

wherein the value indicative for the binding and/or functional interaction is determined by TR-FRET detection.

In a further embodiment the method for determining a binding and/or functional interaction comprises the following steps:

(a) forming a composition of matter comprising the protein of interest and the nucleosomal substrate;

(b) determining a value indicative for the binding and/or functional interaction of the protein of interest with the nucleosomal substrate;

wherein at least one of the histone types of the nucleosomal substrate has a homogenous post-translational modification pattern;

wherein the value indicative for the binding and/or functional interaction is determined by TR-FRET detection;

wherein the protein of interest and the nucleosomal substrate are labeled with corresponding FRET donor and acceptor reporter dyes.

In a specific embodiment, step (a) may be preceded by a step of providing the nucleosomal substrate.

In a further embodiment the method for determining a binding and/or functional interaction comprises the following steps:

(a) forming a composition of matter comprising the protein of interest and the nucleosomal substrate;

(b) determining a value indicative for the binding and/or functional interaction of the protein of interest with the nucleosomal substrate;

wherein at least one of the histone types of the nucleosomal substrate has a homogenous post-translational modification pattern;

wherein the value indicative for the binding and/or functional interaction is determined by TR-FRET detection;

wherein the protein of interest and the nucleosomal substrate are labeled with corresponding FRET donor and acceptor reporter dyes.

In a specific embodiment the method for determining a binding and/or functional interaction comprises the following steps:

(a) forming a composition of matter comprising the protein of interest and the nucleosomal substrate;

(b) determining a value indicative for the binding and/or functional interaction of the protein of interest with the nucleosomal substrate;

wherein at least one of the histone types of the nucleosomal substrate has a homogenous post-translational modification pattern;

wherein the value indicative for the binding and/or functional interaction is determined by FRET detection;

wherein the protein of interest is a posttranslational modifier.

In a specific embodiment the method for determining a binding and/or functional interaction comprises the following steps:

providing of truncated histones;

providing peptides corresponding to the truncated region of the truncated histone;

ligating a truncated histone and the modified peptide corresponding to the truncated region of the truncated histone, thereby obtaining a histone having a homogenous post-translational modification pattern;

combining 4 different histone types, wherein at least one histone type has a homogenous post-translational modification pattern, thereby obtaining histone octamers;

combining DNA with the histone octamers thereby obtaining the nucleosomal substrate;

forming a composition of matter comprising the protein of interest and the nucleosomal substrate;

combining DNA with the histone octamers thereby obtaining the nucleosomal substrate;

determining a value indicative for the binding and/or functional interaction of the protein of interest with the nucleosomal substrate;

wherein at least one of the histone types of the nucleosomal substrate has a homogenous post-translational modification pattern;

In a specific embodiment the method for determining a binding and/or functional interaction comprises the following steps:

providing of truncated histones;

providing peptides corresponding to the truncated region of the truncated histone;

ligating a truncated histone and the modified peptide corresponding to the truncated region of the truncated histone, thereby obtaining a histone having a homogenous post-translational modification pattern;

combining 4 different histone types, wherein at least one histone type has a homogenous post-translational modification pattern, thereby obtaining histone octamers;

combining DNA with the histone octamers thereby obtaining the nucleosomal substrate;

forming a composition of matter comprising the protein of interest and the nucleosomal substrate;

combining DNA with the histone octamers thereby obtaining the nucleosomal substrate;

determining a value indicative for the binding and/or functional interaction of the protein of interest with the nucleosomal substrate;

wherein at least one of the histone types of the nucleosomal substrate has a homogenous post-translational modification pattern;

wherein in ligating step MPAA is added;

wherein in ligating step a buffer without dissolved oxygen is used;

wherein the pH in the ligating step is kept at 7.05;

wherein the value indicative for the binding and/or functional interaction is determined by TR-FRET detection;

wherein determining a value indicative for the binding and/or functional interaction comprises measuring fluorescence in a range of 610 nm to 630 nm and in a range of 650 nm to 690 nm, such as 660nm to 680nm, for example 665 nm or 672 nm.

In a specific embodiment the method for determining a binding and/or functional interaction comprises the following steps:

providing of truncated histones;

providing peptides corresponding to the truncated region of the truncated histone;

ligating a truncated histone and the modified peptide corresponding to the truncated region of the truncated histone, thereby obtaining a histone having a homogenous post-translational modification pattern;

combining 4 different histone types, wherein at least one histone type has a homogenous post-translational modification pattern, thereby obtaining histone octamers;

combining DNA with the histone octamers thereby obtaining the nucleosomal substrate;

forming a composition of matter comprising the protein of interest and the nucleosomal substrate;

combining DNA with the histone octamers thereby obtaining the nucleosomal substrate;

determining a value indicative for the binding and/or functional interaction of the protein of interest with the nucleosomal substrate;

wherein at least one of the histone types of the nucleosomal substrate has a homogenous post-translational modification pattern;

wherein in ligating step MPAA is added;

wherein in ligating step a buffer without dissolved oxygen is used;

wherein the pH in the ligating step is kept at 7.05;

wherein the value indicative for the binding and/or functional interaction is determined by TR-FRET detection;

wherein determining a value indicative for the binding and/or functional interaction comprises measuring fluorescence at 620 nm and 665 nm.

Embodiment Examples 1.1. Bacterial Expression

A single colony of BL21 (DE3) RIL cells was used to inoculate a 2 mL pre-culture of LB medium containing the respective antibiotic. After 8 h incubation, this colony was used to inoculate 6L of ZYM5052 auto inducing medium (Studier et al. 2005; Protein Expression and Purification 41 (2005) 207-234). After growth over-night at 37° C., the cells were harvested by centrifugation for 10 min at 6000×g in a Sorvall Evolution centrifuge using a SLC-6000 rotor.

1.2. Histone Inclusion Body Purification

This protocol describes the production of histone proteins from 2 L of *E.Coli* culture. The denaturing purification of histone proteins was essentially performed as documented in (Luger, K., Rechsteiner, T. J., and Richmond, T. J. (1999). Methods Enzymol 304, 3-19.), with some modifications as described in the follwing: Plasmids encoding histone protein types H2A (GeneBank: CAD89676), H2B (GeneBank: CAD89678), H3 (GeneBank: CAD89679), and H4 (GeneBank: CAD89677) from *X. laevis* were ordered as codon optimized DNA sequences from GencArt (Regensburg, Germany). Bacteria were transduced with plasmid encoding individual histones and homogenized in Wash Buffer (50 mM TrisCl pH=7.5, 100 mM NaCl, 1 mM EDTA, 2 mM DTT, 0.2 mM DTT) by sonication at 4° C. using a Branson Ultrasound sonifier device. Inclusion bodies were pelleted by centrifugation for 20 min at a speed of 15.000×g. The pellet was washed two times with TW Buffer (Wash Buffer with 1% (v/v) Triton X-100) and two times with Wash Buffer. The pellet was flash-frozen in liquid nitrogen and stored at −80° C. for histone purification.

To solubilize the histones from inclusion body pellets, 350 µL DMSO was added to the frozen pellet, followed by 30 min incubation at RT. Then, 13.3 mL unfolding buffer (7 M guanidine-HCl, 20 mM TrisCl pH=7.5, 10 mM DTT) was added and the solution was rotated for 1 h at RT. Insoluble material was removed by centrifugation for 10 min at 23000×g and 4 C.

1.3 Chromatographic Purification of Histones

The supernatant from 1.1 was dialyzed against three changes of 2 L each of Urea Dialysis Buffer (7 M Urea, 1 mM EDTA, 10 mM TrisCl, pH=7.5, 100 mM NaCl, 2 mM DTT, 0.2 mM PMSF) over 5 h. For all buffers containing urea, we prepare buffers from 10M Urea stock solutions that are prepared freshly and arc de-ionized using mixed ion exchange resins until the conductivity of the solution is >0.5 µS to prevent carbamylation of histone proteins during purification.

An XK26/20 Q sepharose column and a XK26/20 SP sepharose column were arranged in tandem and equilibrated in 90% Urea Buffer A (7 M Urea, 10 mM TrisCl pH =7.5, 1 mM EDTA, 2 mM DTT, 0.2 mM PMSF), 10% Urea Buffer B (Urea Buffer A with 1 M NaCl). The dialyzed protein was loaded at a constant flow rate of 2 mL/min and washed with 5 column volumes buffer. The Q sepharose column with the bound DNA and contaminating proteins was removed and the histones eluted with an isocratic gradient from 10 to 100% Urea Buffer B. Fractions were analyzed by SDS-PAGE, pooled, adjusted to 0.01% TFA, 10% Acetonitrile and loaded onto a preparative C-18 reversed phase chromatography columns (Phenomcnex). After extensive washing using 10% Acetonitrile, 90% H2O, 0.01% TFA, the histones were eluted from the column using an isocratic gradient towards 100% acetonitrile, 0.01% TFA. Histones purified by this method were lyophilized as their respective TFA salts and stored at −80° C.

1.4 Generation of modified histones by Native Chemical Ligation

A truncated version of the histone to be modified was obtained as a synthetic gene from GeneArt and the histone prepared from *E.Coli* according to 1.1. As an example H3 (H3 Δ1-20, A21C) is mentioned.

The modified histone tail peptide was synthesized by a conventional Fmoc/But strategy using a specialized SEA-PS resin (bis(2-SulfanylEthyl)Amino-trityl-polystyrene) (Iris GmbH, Germany), incorporating the modified amino acids corresponding to the post-translational modification of interest at the desired position. After cleavage from the resin, the terminus of the peptide is modified by oxidation to SEAoff using DMSO at pH=7.4.

An optimized protocol for preparation of the ligation buffer was established to ensure that no dissolved oxygen remains in the solution, which may reduce the yields dramatically. Also, the non-odorous and less toxic thiol MPAA was introduced to facilitate the ligation reaction.

Buffer R (3M Guanidine, 0.1M Sodium Phosphate, pH=7.3, 50 mM MPAA, 20 mM TCEP) was prepared by mixing all buffer components, followed by careful degassing for 45 min using a flow of helium applied through a needle while stirring the solution vigorously using a magnetic stir bar. The so prepared buffer was protected from environmental oxygen by application of a layer of argon.

Then, the truncated histone was mixed with the synthetic peptide at a 1:1.3 molar ratio in buffer R. After addition of the Histone and Peptide, the pH was rc-adjusted to 7.05 using 10 M NaOH and argon re-applied to the reaction tube. The careful adjustment of the pH may ensure a high reaction yield. The reaction was then allowed to proceed for 24 h at 22° C.

The reaction mixture was diluted 50 fold in SAU-200 buffer (20 mM Sodium-acetate pH=5.2, 1 mM EDTA, 1 mM DTT, 200 mM NaCl, 7 M Urea) and loaded onto a 5 mL HiTrap SP column (GE-Healthcare). Separation of the ligation product was achieved by a linear gradient from SAU-200 to SAU-600 (SAU 200 but 600 mM NaCl). Fractions containing the ligated product were pooled, and purified by C-18 HPLC as described before.

1.5 Preparation of DNA Templates for Chromatin Reconstitution

For reconstitution of mono- and oligonucleosomes, the non-natural nucleosome positioning sequence "601" was used in order to generate high affinity binding sites for the histone octamers (Lowary, P. T., and Widom, J. (1998). J Mol Biol 276, 19-42; Thastrom, A., Lowary, P. T., Widlund, H. R., Cao, H., Kubista, M., and Widom, J. (1999). J Mol Biol 288, 213-229). A 187 bp DNA template for reconstitution of mononucleosomes was generated by digesting a plasmid containing 187 bp long 601 repeats (synthetic construct from GeneArt). DNA was prepared using the Plasmid Giga Kit (Qiagen) according to the manufacturers protocol. After digestion with BsoB1 for 187x601 or amplification by PCR using primers that contain fluorescent dyes at the 5' end (Sigma Aldrich), the fragments were recovered by sequential PEG precipitation as described previously (Lis, J. T., and Schleif, R. (1975). Nucleic Acids Res 2, 383-389.). For longer chromatin stretches, multiple repeats of the 147-201 bp nucleosome positioning sequence were obtained as synthetic genes from GeneArt.

2. In Vitro Chromatin Reconstitution & Analysis 2.1 Histone Octamer Reconstitution The reconstitution of histone octamers was essentially performed according to (Luger, K., Rechsteiner, T. J., and Richmond, T. J. (1999). Methods Enzymol 304, 3-19.), with modifications as introduced by Proteros. In brief, the lyophilized histones were dissolved in unfolding buffer (see 1.1) and mixed in equimolar amounts according to their UV absorbance. After extensive dialysis against three changes of RB high buffer (10 mM TrisCl pH=7.5, 1 mM EDTA, 2 M NaCl, 1 mM DTT), the dialyzed sample was concentrated and subjected to gel-filtration on a HR26/60 Superdex 200 column (GE-Healthcare) in RB high buffer. Fractions containing all four histones were identified by SDS-PAGE, pooled and concentrated. The octamers were either used immediately or diluted 1:1 with 100% glycerol and stored at −20° C.

2.2 Reconstitution of Mono- and Oligonucleosomes

In order to assemble regularly spaced nucleosomes on DNA, a modified method of continuous dialysis adapted from (Luger, K., Rechsteiner, T. J., and Richmond, T. J. (1999). Methods Enzymo1304, 3-19) was applied. In order to obtain a high homogeneity of the nucleosome preparation for the imaging assays, a method to reproducibly generate mg quantities of nucleosomes with lowest batch-to-batch variability was developed.

For a test-assembly, the reconstituted octamers from 2.3 were mixed with DNA in a 0.9:1, 1:1 and 1.2:1 (octamer/DNA) molar ratio in RB high. The concentration of the octamer was determined photometrically assuming that an OD276=0.45, corresponds to 1 mg/ml of histone octamcr. Typically, 20-50 µg of DNA was reconstituted in 500 µl RB high. The dialysis vessels were placed in 400 mL RB high and the buffer was exchanged against 2 1 RB low (RB high but 10 mM NaCl) using an HPLC pump and a specialized beaker to allow for a constant dialysis volume of 400 mL during the reconstitution. The material was then dialyzed against TEA 20 (10 mM triethanolamine-Cl pH=7.5, 20 mM NaCl, 0.1 mM EDTA) and analyzed by native agarose gel electrophoresis and analytical ultracentrifugation. Typically, a ratio of 0.9 to 1 resulted in saturated but not aggregated material. The ratio that was determined in the pre-assembly was then used to produce large quantities using the same device and buffer system as described before.

2.3 Analytical Ultracentrifugation

For analysis by the sedimentation velocity method (Schuck, P. (2000). Biophys J 78, 1606-1619.), 0.3-1 OD260 of oligo- or mononucleosomes were prepared in 400 µl TEA 20. Double-sector charcoal filled epon cells were filled with 412 µl of TEA 20 in the buffer sector and 392 µL chromatin in the sample sector at 20° C. After loading of the rotor, the centrifuge (Beckmann XL-A) was assembled and the vacuum turned on to allow for a 1-2 h temperature equilibration prior to starting the run. For 12 mer oligonucleosomes, a speed of 15.000 rpm and for mononucleosomes a speed of 35.000 rpm was used for sedimenting the molecules within 50-80 scans. During the run, scans were continuously acquired until all material was at the bottom of the cell. The analysis was performed with the SEDFIT software (Schuck, P. (2000). Biophys J 78, 1606-1619.) using a partial specific volume of 0.69 for chromatin. Generally, after positioning the meniscus and the bottom, a simplex fit for the meniscus position was performed at a resolution of 50. The frictional ratio was fitted with the simplex algorithm. The initial values were further refined by fitting with the marquard-levenberg and simulated annealing mechanisms until the root mean square deviation converged at a minimum. Figures of the analytical ultracentrifugation (AUC) analyses were prepared by exporting the raw data at a resolution of 200 to the Origin software (OriginLab).

2.4 FRET Assay:

GST-LSD-1 was purchased from BPS biosciences and H3K36me3 modified nucleosomes were made by Proteros Biostructures GmbH as described above. Anti-double stranded DNA antibody (mouse, monoclonal) was bought from Chemicon (MAB1293). Anti-histone H2B antibody (mouse, monoclonal) was bought from Abeam (mAbcam 52484). Anti-GST-Terbium (monoclonal) was bought from Cisbio bioassays (61GSTTLB). DyLight 650 microscale antibody labeling kit (62266) and dye removal columns (22858) were bought from Thermo Scientific. Dialysis tubes (D-tube dialyzer mini, MWCO 6-8 kd, 71504) were bought from EMD Millipore.

Antibody labeling: anti-double stranded DNA antibody and H2B antibody were labeled with DyLight 650 antibody labeling kit (Thermo scientific) according to manufactures instructions. Excess dye was removed first by dye removal columns and then by dialysis (100 ul) in PBS using dialysis tubes at 4° C. for 2 times 1 hour, followed by overnight dialysis (all 300 mL): Labeling efficiency was determined by absorption measurement at 280 nm (protein conc.) and 650 nm (dye absorption) using a nanodrop device.

Interaction screening: Working stock solutions were made for anti-GST-Tb, anti-dsDNA-dylight 650 (or anti-H2B-dylight 650) and nucleosomes (K36me3). GST-LSD1 was added to the anti-GST-Tb stock solutions at a set concentration. Solutions were pipetted in a low volume, low binding black 384 well plate, 3 µL per stock solution to a total volume of 9 µL per well. The plate was spun for 30 seconds at 500 rpm, followed by 10 min incubation at RT. Next, the plate was exposed to light of 340 nm and fluorescence was measured at 620 nm and 655 nm using a PHERAstar microplate reader (BMG Labtech) at 25 degrees. Measurements were done in cycles, 15 in total and 3 minutes in between each cycle. TR-FRET delay was set to 65 µs.

The screening confirmed that the LSD-1 protein and the nucleosome are in close enough proximity to yield a clearly detectable FRET signal. This indicates specific binding of LSD1 to the recombinant nucleosome. Comparison of the two different antibodies showed that the double stranded DNA antibody gives a better signal. Possibly this is due to the difference in available binding sites. The H2B antibody has only two potential binding sites per nucleosome, while the double stranded DNA antibody has virtually unlimited binding sites, as long as there is still room on the DNA.

3. Assessment of Chromatin Compaction Status:

3.1 Attachment of FRET Donor and FRET Acceptor to the Nucleosomal Substrate to Measure Chromatin Compaction:

Towards this end, PCR was used to generate a nucleosomal DNA template tabled on the 5' end with a FRET donor molecule Atto 550. In brief, two DNA templates were made with the following templates and primers:

```
Control template (SEQ ID NO.: 3):
5'-
GTTATGTGATGGACCCTATACGCGGCCGCCCTGGAGAATCCCGGTGCCGA
GGCCGCTCAATTGGTCGTAGCAAGCTCTAGCACCGCTTAAACGCACGTAC
GCGCTGTCCCCCGCGTTTTAACCGCCAAGGGGATTACTCCCTAGTCTCCA
GGCACGTGTCAGATATATACATCCTGTGCATGTATTGAACAGCGACTCGG
GTTATGT-3'.

Remodeling template (SEQ ID NO.: 4):
5'-
CTGGAGAATCCCGGTGCCGAGGCCGCTCAATTGGTCGTAGCAAGCTCTAG
CACCGCTTAAACGCACGTACGCGCTGTCCCCCGCGTTTTAACCGCCAAGG
GGATTACTCCCTAGTCTCCAGGCACGTGTCAGATATATACATCCTGTGCA
TGTATTGAACAGCGACTCGGGTTATGTGATGGACCCTATACGCGGCCGCC
CTGGAGA-3'.

Primers:
Control DNA:
FW (SEQ ID NO.: 5):
Atto550-5'-GTTATGTGATGGACCCTATACGC-3';

Rev (SEQ ID NO.: 6):
5'-ACATAACCCGAGTCGCTGTTCA-3'.

Remodeling template:
FW (SEQ ID NO.: 7):
Atto550-5'-CTGGAGAATCCCGGTGCC-3';

Rev (SEQ ID NO.: 8):
5'-TCTCCAGGGCGACCG-3'.
```

PCR reactions were done according to the following protocols: Control DNA, per reaction of a 100 µL contained: 4 µL template DNA (10 pg/µL), 2 µL dNTP solution (NEB, 10 mM per nucleotide), 1 µL primer mix (10 µM per primer), 0.5 µL TAQ polymerase (NEB, 5000 units/mL), 104 10× standard TAQ reaction buffer (NEB) and 82.5 µL ddH$_2$O. PCR program: preheat lid to 95° C., start-1 min 95° C., cycle-30 sec 95° C., 30 sec 54° C., 30 sec 68° C.-30 repeats. Finish-1 min 68° C., 4° C. until collection of plates. Remodeling DNA, per reaction of a 100 µL contained: 4 µL template DNA (10 pg/µL), 2 ∞L dNTP solution (NEB, 10 mM per nucleotide), 2 µL primer mix (10 µM per primer), 0.5 µL TAQ polymerase (NEB, 5000 units/mL), 104 10× standard TAQ reaction buffer (NEB) and 81.5 µL ddH$_2$O. PCR program: preheat lid to 95° C., start-1 min 95° C., cycle-30 sec 95° C., 30 sec 60° C., 30 sec 68° C.-30 repeats. Finish-1 min 68° C., 4° C. until collection of plates. Reaction mixes were pooled and precipitates with ethanol. $\frac{1}{10}^{th}$ volume of 3M NaAc was added (final concentration 0.3M NaAc), followed by 1.5 volumes of 100% EtOH chilled to −80° C. Mixture is briefly shaken and incubated for 20 min at −20° C., followed by 15 min centrifugation at 4000 rpm, 15 min, 4° C. Supernatant is removed, pellet washed once with 70% ethanol, followed by centrifugation (4000 rpm, 5 min, RT) and air dried. Pellet was resuspended in ddH$_2$O and purified with a superdex 200 size exclusion column. Fractions were checked for correct size DNA with a 1.5% agarose gel and SYBRsafe (Lifetech) for staining. Fractions containing only correct size DNA were pooled and precipitated with ethanol as described above. After drying, pellet was resuspended in ddH$_2$O and a small fraction put on agarose gel (1.5%) against known quantity control DNA for quantification.

To complete the FRET pair, histone octamers were reconstituted using histone H2B carrying a FRET acceptor Atto 647N. To afford labeled H2B, a single cysteine residue was introduced at position 120 and the protein was expressed and purified as described before. Labeling of the cysteine residue was performed by first reducing through the addition of 25mM TCEP in buffer (7M Guanidine HCL, 20 mM TRIS-Cl pH 7.0 and 5 mM EDTA), followed by desalting using a PD10 gel filtration column. A 2 fold molar excess of Atto 647N-Maleimide was added to the purified and reduced histone as a DMSO solution, followed by incubation at room temperature for 2h in the dark. Next, unreacted dye was inactivated through the addition of 25 mM beta-mercaptoethanol and the reaction mixture was purified using a PD10 column primed with buffer 2 (7M Guanidine HCL, 20 mM TRIS-Cl pH 7.5 and 10 mM DTT). The labeled histone was lyophilized to be used in octamer reconstitutions as described in 2.1. The DNA template from and the histone octamer containing labled H2B were reconstituted into nucleosomes according to 2.2.

3.2 Measuring Chromatin Compaction by Intramolecular FRET on Nucleosomal Templates The measurement of the sliding of a nucleosome along a DNA strand by remodeling of nucleosomes was measured using FRET. As basis for the procedure components from a chromatin assembly kit (active motif, cat #53500) were used.

Figure 1:
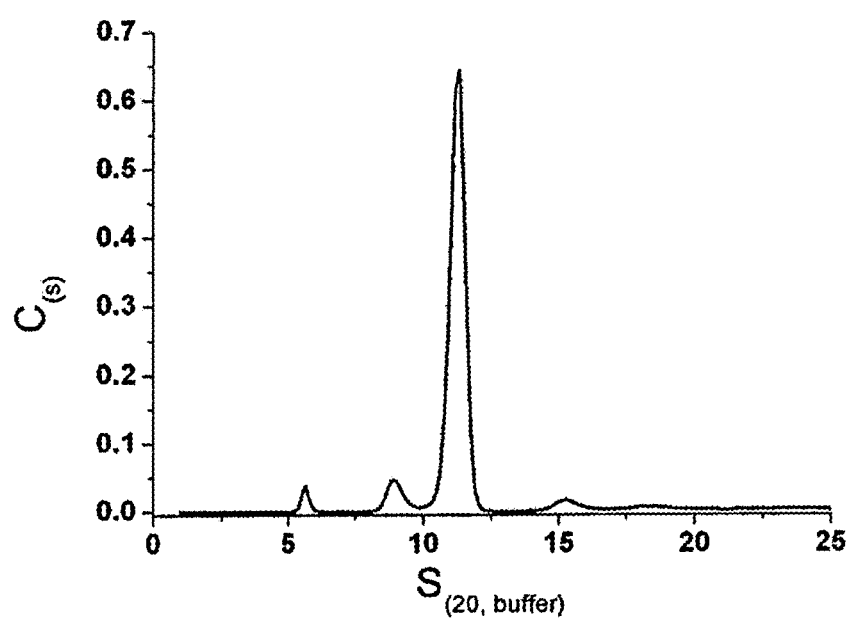
FIG. 1. AUC analysis of prepared nucleosomes.

The following reaction mixture was made with components from the chromatin assembly kit for a 100 µL reaction. 10 µL high salt buffer, 64.3 µL low salt buffer, 13.2 µL ddH$_2$O, 10 µL 10× ATP and 2.5 µL ACF complex. The mixture was pipetted up and down a few times to mix. In a black 384 well plate (NUNC, round bottom, low volume), 1 µL of the nucleosome assembled with either the control DNA or the remodeling DNA was added to the wells, followed by the addition of 8 µL of the reaction mixture. The plate is then immediately transferred to a PHERAstar microplate reader (BMG Labtech). The plate was exposed to light of 540 nm and fluorescence was measured at 590 nm and 680 nm at 25 degrees. Excitation was done with the laser and with 40 flashes per well. Measurements were done in cycles, 15 in total and 20 seconds in between each cycle. . The results are shown in FIG. 1b.

The chromatin compaction works via HP1 proteins binding Histone H3 Lys9 methylated nucleosomes. HP1 proteins dimerize when bound to nucleosomes and pulls the nucleosomes in close proximity of each other (see FIG. 6). The increasing close proximity of FRET acceptors on the nucleosomes to the FRET donor on the DNA means the FRET signal increased when the chromatin becomes more condensed (see FIG. 5).

Histone octamers with H3K9 methylation are prepared as described above labeled with a FRET acceptor, while DNA is labeled at one 5 prime end as described above, with a larger DNA template (12× histone binding sequence SEQ ID NO.:2). DNA and nucleosome are assembled into chromatin as described above. A reaction mixture is made, containing buffer with 20 mM or less NaCl/KCland HP1. In a black 384 well plate (NUNC, round bottom, low volume), 1 µL of the assembled chromatin is pipetted per well. 8 µL is added of the reaction mixture. The plate is placed into a PHERAstar microplate reader (BMG Labtech) at 37° C. The plate is exposed to light of 540 nm and fluorescence is measured at 590 nm and 680 nm at 37° C. degrees. Excitation is done with the laser. Measurements is done in cycles, at least 30 with 30 seconds between each cycle.

The following embodiments of the invention are numbered as embodiments 1 to 39 and relate to:

1. Method for determining a binding and/or functional interaction of a protein of interest with a nucleosomal substrate comprising DNA wrapped around histone octamers, wherein the method comprises the following steps:
    (a) forming a composition of matter comprising the protein of interest and the nucleosomal substrate;
    (b) determining a value indicative for the binding and/or functional interaction of the protein of interest with the nucleosomal substrate;
    wherein at least one histone type of the nucleosomal substrate has a homogenous post-translational modification pattern.

2. Method according to embodiment 1,
    wherein the value indicative for the binding and/or functional interaction is determined by optical detection, optionally fluorescent detection.

3. Method according to embodiment 2,
    wherein fluorescent detection is FRET detection, optionally TR-FRET detection.

4. Method according to any of the preceding embodiments,
    wherein the composition of matter further comprises a molecule which is a candidate for modulating the binding and/or functional interaction of the protein of interest with the nucleosomal substrate.

5. Method according to any of the preceding embodiments,
    wherein each of the histone types has a homogenous post-translational modification pattern.

6. Method according to any of the preceding embodiments,
    wherein the DNA wrapped around histone octamers is arranged in mononucleosomes and/or oligonucleosomes.

7. Method according to any of the preceding embodiments,
    wherein the method is carried out in medium to high through-put format, optionally in high through-put format.

8. Method according to embodiment 7,
    wherein the method is carried out in 96, 384 or 1536 well plates.

9. Method according to any of the preceding embodiments,
    wherein the nucleosomal substrate is labeled, optionally wherein the DNA and/or the histones of the nucleosomal substrate are labeled.

10. Method according to any of the preceding embodiments,
    wherein the value indicative for the binding and/or functional interaction depends on the compaction state of the nucleosomal substrate.

11. Method according to any of the preceding embodiments,
    wherein the protein of interest is labeled with a fluorescent label.

12. Method according to embodiment 11,
    wherein the protein of interest is labeled with a FRET acceptor and the nucleosomal substrate is labeled with a corresponding FRET donor.

13. Method according to embodiment 11,
    wherein the protein of interest is labeled with a FRET donor and the nucleosomal substrate is labeled with a corresponding FRET acceptor.

14. Method according any of embodiments 1 to 9,
    wherein the composition of matter further comprises a reporter protein capable of recognizing a histone having a post-translational modification.

15. Method according to embodiment 14,
wherein the reporter protein is an antibody or a histone binding domain.

16. Method according to embodiment 14 and 15,
wherein the reporter protein is labeled, optionally fluorescently labeled.

17. Method according to any of embodiments 14 to 16,
wherein the reporter protein is labeled with a FRET acceptor and the nucleosomal substrate is labeled with a corresponding FRET donor, or the reporter protein is labeled with a FRET donor and the nucleosomal substrate is labeled with a corresponding FRET acceptor.

18. Method according to any of the preceding embodiments,
wherein the protein of interest is an epigenetic regulator.

19. Method according to embodiment 18,
wherein the epigenetic regulator is a post-translational modifier.

20. Method according to any of the preceding embodiments,
wherein step (a) is preceded by a step of providing the nucleosomal substrate.

21. Method according to embodiment 20, wherein the step of providing the nucleosomal substrate is the method of embodiments 22 to 33.

22. Method for providing a nucicosomal substrate comprising DNA wrapped around histone octamers, wherein the method comprises the following steps:
(a) providing histone octamers wherein at least one of the histone types of the histone octamer has a homogenous post-translational modification pattern;
(b) combining DNA with the histone octamers thereby obtaining the nucleosomal substrate.

23. Method according to embodiment 22,
wherein the method further comprises labeling the nucleosomal substrate.

24. Method according to embodiment 22 and 23,
wherein labeling the nucleosomal substrate comprises labeling DNA, optionally via PCR and/or by ligation of labeled oligonucleotides, and/or labeling at least one of the histone types;

25. Method according to any of embodiments 22 to 24,
wherein the at least one histone type having a homogenous post-translational modification pattern is provided by total chemical synthesis.

26. Method according to any of embodiments 22 to 24,
wherein the at least one histone type having a homogenous post-translational modification pattern is provided by site-specific incorporation of an amino acid analogue, optionally by site-specific incorporation of a methyl lysine analogue and/or an acetyl-lysine analogue.

27. Method according to any of embodiments 22 to 24,
wherein the at least one histone type having a homogenous post-translational modification pattern is provided by the method comprising the following the steps:
(i) providing truncated histones of a histone type;
(ii) providing peptides having a homogenous post-translational modification pattern;
(iii) ligating the truncated histones of step (i) and the peptides of step (ii).

28. Method according to embodiment 27,
wherein step (i) comprises site-specific incorporation of an amino acid analogue, optionally site-specific incorporation of a methyl lysine analogue and/or acetyl-lysine analogue.

29. Method according to embodiment 27 and 28,
wherein in step (ii) the peptide is produced by chemical synthesis.

30. Method according to any of embodiments 27 to 29,
wherein the truncated histone comprises an affinity tag and/or a fluorescent tag.

31. Method according to any of embodiments 27 to 30,
wherein the truncated histone is truncated at the C-terminal region and the peptide comprises a C-terminal region of the full-length histone.

32. Method according to any of embodiments 27 to 30,
wherein the truncated histone is truncated at the N-terminus and the peptide comprises an N-terminal region of the full-length histone.

33. Method according to any of embodiments 27 to 32,
wherein the peptide comprises a histone tail peptide.

34. Nucleosomal substrate comprising DNA wrapped around histone octamers,
wherein at least one of the histone types of the nucleosomal substrate has a homogenous post-translational modification pattern.

35. Nucleosomal substrate according to embodiment 34,
wherein each of the histone types has a homogenous post-translational modification pattern.

36. Nucleosomal substrate according to embodiment 34 and 35,
wherein the DNA sequence is predetermined.

37. Nucleosomal substrate according to any of embodiments 34 to 36,
wherein the DNA wrapped around histone octamers is arranged in mononucleosomes and/or oligonucleosomes.

38. Nucleosomal substrate according to any of embodiments 34 to 37,
wherein the nucleosomal substrate is fluorescently labeled.

39. Nucleosomal substrate according to any of embodiments 34 to 38,
wherein the DNA and/or at least one of the histone types is fluorescently labeled.

The invention claimed is:

1. A method for determining a binding and/or functional interaction of a protein of interest with a nucleosomal substrate comprising DNA wrapped around histone octamers, wherein the method comprises:
   (a) forming a composition comprising the protein of interest and the nucleosomal substrate; and
   (b) determining a value indicative for the binding and/or functional interaction of the protein of interest with the nucleosomal substrate by FRET detection;
wherein at least one histone type of the nucleosomal substrate has a homogenous post-translational modification pattern,
   wherein the protein of interest is labeled with a FRET acceptor and the nucleosomal substrate is labeled with a corresponding FRET donor or wherein the protein of interest is labeled with a FRET donor and the nucleosomal substrate is labeled with a corresponding FRET acceptor, and
   wherein the protein of interest is an epigenetic regulator.

2. The method of claim 1, wherein the FRET detection is TR-FRET detection.

3. The method of claim 1, wherein the composition further comprises a molecule which is a candidate for modulating the binding and/or functional interaction of the protein of interest with the nucleosomal substrate.

4. The method of claim 1, wherein the DNA wrapped around histone octamers is arranged in oligonucleosomes.

5. The method of claim 1, wherein the DNA of the nucleosomal substrate is labeled with a FRET donor and/or FRET acceptor.

6. The method of claim 1, wherein the histones of the nucleosomal substrate are labeled with a FRET donor and/or FRET acceptor.

7. The method of claim 1, wherein the composition further comprises a reporter protein capable of recognizing a histone having a post-translational modification.

8. The method of claim 7, wherein the reporter protein is an antibody.

9. The method of claim 7, wherein the reporter protein is a histone binding protein.

10. The method of claim 9, wherein the histone binding protein is a histone binding domain or a protein containing a histone binding domain.

11. The method of claim 10, wherein the histone binding domain is a BROMO-, CHROMO- and/or PHD finger domain.

12. The method of claim 9, wherein the histone binding protein is selected from the group comprising MLL1/2, MLL3/4, SMYD3, USP22, G9A, HP1, JMJD2a, JMJD2c, BRD4, SMARCA2, p300, EZH2, JARID1a, JARID 1b, SetD8, PADI4, PHF8, PRMT5, SetDB8, NSD1, NSD2, NSD3, FBXL10, JMJD3, Dot1L, LSD1, HDAC1-11, Sirtuin 1-7, Tip60, PCAF, UTX, EZH1, PRMT3, PRMT4 d USP16.

13. The method of claim 12, wherein the histone binding protein is selected from the group comprising EZH2, SMYD3, JMJD3, BRD4, NSD2, LSD1, HDAC2 and HDAC6.

14. The method of claim 1, wherein the value indicative for the binding and/or functional interaction depends on the compaction state of the nucleosomal substrate.

15. The method of claim 4, wherein the value indicative for the binding and/or functional interaction depends on the compaction state of the nucleosomal substrate, and wherein several nucleosomes of the oligonucleosomes are labeled.

* * * * *